United States Patent [19]
Kojima et al.

[11] Patent Number: 5,443,711
[45] Date of Patent: Aug. 22, 1995

[54] OXYGEN-SENSOR ELEMENT

[75] Inventors: Takao Kojima; Hiroyuki Ishiguro; Masaru Yamano; Noriaki Kondo; Masahiko Yamada; Toshiki Sawada, all of Aichi, Japan

[73] Assignee: NGK Spark Plug Co., Ltd., Aichi, Japan

[21] Appl. No.: 997,137

[22] Filed: Dec. 22, 1992

Related U.S. Application Data

[63] Continuation of Ser. No. 429,938, Nov. 1, 1989, abandoned.

[30] Foreign Application Priority Data

Dec. 2, 1988 [JP] Japan .................. 63-306279

[51] Int. Cl.⁶ .................................. G01N 27/417
[52] U.S. Cl. .................. 204/429; 204/426; 204/427; 427/126.3
[58] Field of Search ............ 204/153.18, 421–429

[56] References Cited

U.S. PATENT DOCUMENTS

| | | | |
|---|---|---|---|
| 3,843,400 | 10/1974 | Radford et al. | 204/421 |
| 3,978,006 | 8/1976 | Topp et al. | 204/429 |
| 3,989,614 | 11/1976 | Tien | 204/426 |
| 4,021,326 | 5/1977 | Pollner et al. | 204/429 |
| 4,097,353 | 6/1978 | Kishida et al. | 204/429 |
| 4,177,112 | 4/1979 | Suzuki | 204/153.18 |
| 4,280,890 | 7/1981 | Friese et al. | 427/123 |
| 4,720,335 | 1/1988 | Fukushima et al. | 204/424 |
| 4,915,080 | 4/1990 | Nakaniwa et al. | 204/426 |

FOREIGN PATENT DOCUMENTS

| | | |
|---|---|---|
| 57-34900 | 7/1982 | Japan . |
| 61-79155 | 4/1986 | Japan . |
| 62-245148 | 10/1987 | Japan . |
| 2200460 | 3/1988 | United Kingdom . |

OTHER PUBLICATIONS

Patent Abstracts of Japan, vol. 4, No. 43 (P-5) [525], 4th Apr. 1980; JP-A-55 13 828 (Toyota) 31 Jan. 1980.
Patent Abstracts of Japan, vol. 8, No. 275 (P-321) [1712], 15th Dec. 1984; JP-A-59 142 455 (Mazda) 15 Aug. 1984.
Kobutsu Kogaku (Mineral Engineering), 5th Ed. by Bunpei Yoshiki, K.K. Gihodo, 1968.
Patent Abstracts of Japan, vol. 4, No. 47 (P-006), 11th Apr. 1980; JP-A-55 20 423 (Toyota) 13 Feb. 1980.
Patent Abstracts of Japan, vol. 2, No. 86 [3821], 14th Jul. 1978; JP-A-53 50 888 (Nippon Denso) 05 Sep. 1978.
Patent Abstracts of Japan, vol. 2, No. 108 [5724], 8th Sep. 1978; JP-A-53 686 (Nippon Denso) 28 Jun. 1978.

*Primary Examiner*—T. Tung
*Attorney, Agent, or Firm*—Fish & Richardson

[57] ABSTRACT

Oxygen-sensor element comprises reference-gas-side and detection-gas-side electrodes on both surfaces of a solid-electrolyte body, and a porous protective layer on the surface of the detection-gas-side electrode, wherein at least a part (including at least a surface layer) of said porous protective layer is formed by a granular texture of a grain size of 0.1 to 0.5 $\mu$m formed mainly of a non-stoichiometric compound of a transition metal oxide ($TiO_x$), and a catalyst for having gas components of the gas to be measured react is carried in at least a part (including at least a surface layer) of the porous protective layer. Oxidation reaction of gas components is improved to prevent deterioration of the responsive property.

55 Claims, 12 Drawing Sheets

OXYGEN-SENSOR ELEMENT

This application is a continuation of U.S. application Ser. No. 07/429,938 filed Nov. 1, 1989, now abandoned.

FIELD OF THE INVENTION

This invention relates to an oxygen-sensor element for detecting oxygen concentration in various kinds of combustion apparatuses, and more particularly, to an oxygen-sensor element for controlling air-to-fuel ratio which is utilized for purifying exhaust gas from an internal combustion engine, and a method of producing the same.

BACKGROUND

Heretofore, in order to control air-to-fuel ratio in internal combustion engines, various kinds of combustion apparatuses and the like, oxygen sensors for detecting oxygen concentration in exhaust gases have been used. As this kind of oxygen sensor, there has been known, for example, a sensor which measures oxygen concentration contained in a detection gas using a solid electrolyte which produces an electromotive force by a difference in oxygen concentration between a reference-gas side and a detection-gas side. The solid electrolyte is an oxygen-ion-conductive material, such as zirconia and the like. It is usually formed into the shape of a test tube or a cylinder, and a reference-electrode-side electrode and a detection-gas-side electrode are formed on its inner surface and outer surface, respectively.

On the surface of the detection-gas-side electrode, a porous protective layer of alumina is formed to protect the electrode. On a surface layer of the porous protective layer, particles of platinum catalyst for promoting the oxidation reaction of gas components are carried in order to detect air-to-fuel ratio with an excellent accuracy (refer to JP Patent Kokoku Publication No. 57-34900 (1982)).

That is, an oxygen-sensor element for controlling air-to-fuel ratio generally comprises a body of an oxygen-ion-conductive solid electrolyte and a pair of electrodes (a reference electrode and a measuring electrode) provided on its inner and outer surfaces, and is covered with a porous protective layer in order to protect the measuring electrode contacting exhaust gases from exhaust gases. In this kind of sensor element, however, excess air factor ($\lambda$) shifts, that is, a so-called $\lambda$-point shift is produced, due to unburnt components included within exhaust gases, and detection accuracy decreases. Various researches and proposals have therefore been done.

For example, an oxygen-sensor element carrying a noble-metal catalyst within a protective layer has been proposed (JP Patent Kokai Publication Nos. 53-50888 (1978), 50-14396 (1975) and 54-89696 (1979)).

Problems to be solved by the Invention

There has been a problem, however, that, when platinum is carried on the above-described protective layer (surface layer), gas components of a detection gas is excessively adsorbed on the platinum having high catalytic property, and the responsive property of the oxygen sensor decreases in some cases due to the adsorbed gases to produce a shift in the control of air-to-fuel ratio. In another example, there has been a problem that platinum particles penetrate into minute pores of the porous protective layer to produce clogging, and the responsive property of the oxygen sensor decreases.

Moreover, there has been a problem in durability. That is, carbon, CO and the like in a detection gas pass through the surface layer in some cases during the application. At this time, carbon is converted into graphite due to the action of the catalyst or the electrode to produce cracks in the porous protective layer, or to produce peeling in some cases. In the worst case, the protective layer peels off, and the electrode is sublimated. When the carried amount of the catalyst is increased, clogging is produced to cause deterioration in response. On the other hand, too small an amount of the catalyst causes dissipation of the catalyst to reduce its effect.

There has also been proposed an oxygen-sensor element which has two protective layers, and in which the catalyst is carried only in a layer disposed on the more outer side (JP Patent Kokai Publication Nos. 53-72686 (1978) and 55-13828 (1980)). In this kind of oxygen-sensor element, however, a catalyst-carrying layer itself easily peels off, and hence catalytic action can not be effectively utilized.

There has further been proposed an oxygen-sensor element comprising a material which occludes and releases oxygen as a protective layer (JP Patent Kokai Publication No. 62-245148 (1987)). However, this element also has the same problem as in the above-mentioned technique that the protective layer easily peels off, and deterioration in durability is also concerned about.

SUMMARY OF THE DISCLOSURE

It is a basic object of the present invention to solve such problems, that is, to develop an oxygen-sensor element which is excellent in durability, which can effectively utilize a noble-metal catalyst, and which can maintain exact control of air-to-fuel ratio for a long period of time without producing a shift in $\lambda$-point and a decrease in responsive property.

It is a particular object of the present invention to develop an oxygen-sensor element which maintains a little richer control, which is the most suitable control state, even at low temperatures no higher than 400° C. (at an initial stage in driving an engine, and the like), and which can contribute to improvement in purification property.

As a result of an intensive research based on such a viewpoint, the present inventor has completed the present invention by further developing the invention disclosed in JP Patent Application No. 63-27623 (1988).

The above-mentioned problems will be solved by the following aspects of the present invention.

(1) 1st Aspect

An oxygen-sensor element comprising a reference-gas-side electrode on one surface of a solid-electrolyte body, a detection-gas-side electrode on another surface, and a porous protective layer on the surface of the detection-gas-side electrode, for measuring the oxygen concentration of a gas to be measured: using an electromotive force produced in accordance with a difference in oxygen concentration between the reference-gas side and the detection-gas side, wherein at least a part (including at least a surface layer) of the porous protective layer is formed by a granular texture formed mainly of a nonstoichiometric compound of transition metal oxide, the granular texture made up of grains having a grain size of 0.1 $\mu$m to 0.5 $\mu$m, and a catalyst for having gas components of the gas to be measured react is carried in at least a part (including at least a surface layer) of the porous protective layer.

(2) 2nd Aspect

An oxygen-sensor element comprising a reference electrode on the side of one surface of a solid-electrolyte body and a measuring electrode on the side of another surface, for detecting an oxygen concentration of a gas to be measured, wherein the solid-electrolyte body comprises a base portion, a protruded portion with protrusions (preferably spherical) directly connected to the base portion, and the measuring electrode at a position including the protruded portion, the measuring electrode is coated with a porous first protective layer, which is coated with a porous second protective layer, and each of the first and second protective layers carries a noble-metal catalyst for promoting the oxidation reaction of the gas to be measured, the first protective layer is formed of a metal oxide which is chemically stable against the gas to be measured, and the second protective layer is formed of a nonstoichiometric transition metal oxide.

(3) 3rd Aspect

An oxygen-sensor element, wherein a solid-electrolyte body comprises a base portion and a protruded portion with protrusions (preferably spherical) connected to the base portion via a measuring electrode (other configurations are identical to those of the above-described Aspect (2)).

(4) 4th Aspect

An oxygen-sensor element comprising a reference electrode on the side of one surface of a solid-electrolyte body and a measuring electrode on the side of another surface, for detecting an oxygen concentration of a gas to be measured, wherein the solid-electrolyte body comprises a base portion, a protruded portion with protrusions (preferably spherical) directly connected to the base portion, and the measuring electrode at a position including the protruded portion, and the measuring electrode is coated with a porous protective layer, and at least a part of the protective layer is formed of a nonstoichiometric transition-metal oxide and carries a noble-metal catalyst for promoting the oxidation reaction of the gas to be measured.

(5) 5th Aspect

An oxygen-sensor element, wherein a solid-electrolyte body has the same configuration as that of the above-described Aspect (3) (other configurations are identical to those of the above-described Aspect (4)).

(6) 6th Aspect

A method of producing an oxygen-sensor element comprising a reference electrode on the side of one surface of a solid-electrolyte body and a measuring electrode on the side of another surface, for detecting an oxygen concentration of a gas to be measured, wherein processing of the side of one surface of a base material of the solid-electrolyte body at least comprises the steps of:

(a) a step for applying particles (preferably generally spherical) of a solid electrolyte on the one surface of a base material of the solid-electrolyte body, (b) a step for depositing an electrode material on the applied surface in step (a), (c) a step for forming a layer of (preferably by flame-spraying) a metal oxide component on the deposited surface in step (b), (d) a step for dipping the applied (preferably flame-sprayed) layer in process (c) in a solution of a noble-metal salt, (e) a step for coating the produced surface in step (d) with a paste-like substance provided by mixing a nonstoichiometric transition-metal-oxide component and a noble-metal component, and (f) a step for subsequently firing the resultant substance in step (e).

(7) 7th Aspect

An oxygen-sensor element, wherein a heater is provided for heating at least a portion relating to the measuring function in the element, in one of the above-described Aspects 1–5 (particularly 2nd Aspect).

In the oxygen sensor according to the first aspect of the present invention, a porous protective layer is formed on the surface of a detection-gas-side electrode of a solid-electrolyte body. A surface layer of the porous protective layer is formed by a nonstoichiometric compound of a transition metal oxide having a predetermined grain size, and a catalyst is further carried on (and in) the surface layer. Accordingly, oxidation reaction of gas components in a Bas to be measured (may be referred to as "detection gas") is sufficiently performed, and the responsive property (i.e., response characteristic) of the sensor is also excellent. Furthermore, it is possible to prevent clogging caused by the presence of the catalyst, and also to prevent decrease in the oxidation reaction of the oxygen sensor due to dissipation of the catalyst and decrease in durability due to gas adsorption and the like. In addition, since penetration of noxious materials, such as carbon and the like, can be effectively prevented, cracks and peeling are not produced in the porous protective layer.

According to the 2nd through 6th aspects of the present invention, since a solid-electrolyte body and a protective layer are firmly bonded together by the presence of a spherically-protruded portion, peeling of the protective layer can be prevented, and hence the sensor is excellent in durability. Furthermore, since excessive adsorption on and reaction with a noble metal of unburnt components can be suppressed by a second protective layer, the sensor is also excellent in responsive property and λ-characteristic (λ: excess air factor), and it is possible to maintain a high-accuracy control of air-to-fuel ratio. Since dissipation of a carried catalyst of a first protective layer is prevented by the second protective layer, the carried amount of the catalyst of the first protective layer can be reduced, and it is possible to maintain more accurate control of air-to-fuel ratio by its catalytic action. Moreover, since, in addition to carried noble-metal catalysts in the first and second protective layers, the second protective layer itself has a catalytic action for promoting the oxidation reaction of unburnt components in a gas to be measured, the entire protective layers can participate in the catalytic action. Hence, volume expansion due to the reaction between the catalyst and the unburnt components can be prevented as much as possible. This fact also contributes to improvement in durability. In addition, even if the noble metal in the second protective layer is sublimated, it is possible to continuously provide a sufficient catalytic action by the carried catalyst of the first protective layer and the second protective layer itself.

According to the 7th aspect of the present invention, since a heater for heating at least a portion relating to the measuring function in the element is provided, variations and change in the lapse of time of air-to-fuel ratio are small especially even at low temperatures no higher than 400° C., and it is possible to easily control toward a targeted air-to-fuel ratio in accordance with the kind of a vehicle and the like.

Accordingly, the present invention can efficiently oxidize unburnt components in a gas to be measured by effectively utilizing an expensive noble metal, and can stably maintain the most suitable sensor control having high accuracy irrespective of low and high temperatures by adding the 7th aspect.

The present invention can thus contribute to a significant improvement in the purification property of exhaust gases by combining ternary catalysts, and is extremely useful in the field of oxygen sensors.

DESCRIPTION OF THE PREFERRED EMBODIMENTS

1st Aspect

In the 1st aspect, the above-described surface layer is provided in various thicknesses in accordance with the shape, the object of application and the like of the oxygen sensor. Especially when the thickness of the protective layer (surface layer) is not less than 5 $\mu$m and not more than 60 $\mu$m, it is possible to protect a layer disposed at more inner side from the surface layer (an inner protective layer) in the porous protective layer and the detection-gas-side electrode from noxious materials, such as carbon and the like, and to properly perform circulation of the detection gas. Hence, an excellent responsive property can be maintained.

If the surface layer is formed centering around the distal end of the solid-electrolyte body, and is formed so that the length of the surface layer is within the range not less than 3/5 and not more than 9/10 from the distal end relative to the length of the portion to be exposed to the detection gas on the detection-gas side of the solid-electrolyte body, this configuration is suitable since it is possible to sufficiently protect the electrodes and the like.

Furthermore, if spherical particles consisting of the same or similar material as the solid-electrolyte body are secured on the outer surface of the above-described solid-electrolyte body, large projections and recesses are produced on the surface, and the detection-gas-side electrode is firmly connected thereto. Hence, peeling and the like are not produced. This configuration is therefore suitable.

In addition, if the catalyst carried in the above-described surface layer is platinum, and the content of the platinum is not less than 0.2 mole % and not more than 5 mole % relative to the surface layer, this configuration is suitable from the viewpoint of promotion of oxidation reaction and improvement in responsive property.

Although the above-described catalyst may be only in the surface layer, it is preferred that the catalyst is carried on the entire porous protective layer.

The entire protective layer may also be formed by a nonstoichiometric compound of a transition metal oxide.

The oxygen sensor of the present invention measures the oxygen concentration of the detection gas side using an electromotive force produced in accordance with the difference between the oxygen concentration at the detection-gas side and the oxygen concentration at the reference-gas side.

In the oxygen sensor of the present aspect, the oxidation reaction of gas components of the detection gas is not only performed by the catalyst carried in the surface layer, but also promoted by the catalytic property which the transition metal forming the surface layer has. In addition, since a nonstoichiometric compound has properties of removing excess oxygen in a gas or releasing oxygen into the gas due to changes in electron holes or defects in accordance with the amount of oxygen, it supplements the above-described oxidation reaction, and prevents excessive adsorption of the gas components on the carried catalyst. The oxidation reaction is thereby promoted, and responsive property is also improved.

Furthermore, since the above-described surface layer has a granular structure, and its grain size of grains making up each granule is not less than 0.1 $\mu$m and not more than 0.5 $\mu$m, it maintains the responsive property of the oxygen sensor at a high value by properly circulating the detection gas, and, at the same time, prevents noxious materials, such as carbon and the like from passing through the surface layer, to prevent formation of graphite from carbon and/or carbon compound which have penetrated and accompanied generation of cracks and peeling in the porous protective layer.

2nd–6th Aspects

The element or solid-electrolyte body may have various shapes, such as a closed tube (a test tube), a plate, a tube and the like, as long as its distal end is closed, there is a space on the inner side, and its rear end is open. Otherwise, a body, in which the distal end is closed, there is a space on the inner side, and the rear end is open, may be separately provided, and respective components, such as a solid-electrolyte body and the like, of the element may be connected to the body to provide a closed tube as the entire element. As a solid-electrolyte material, a material provided by adding $Y_2O_3$, CaO and the like to $ZrO_2$ as stabilizers may, for example, be used. Both the reference electrode and the measuring electrode (laminar) are made porous, and noble metal such as Pt or Pt including not more than 2% of Rh or the like may be used.

Another surface (a surface on which the measuring electrode is to be formed) of the solid-electrolyte body is provided as a spherically-protruded portion of a solid electrolyte. This is for providing a state in which the spherically-protruded portion is penetrated in the measuring electrode and further in the protective layer in the shape of an edge, to firmly and physically connect together the solid-electrolyte body and the protective layer. Due to the presence of the spherically-protruded portion, even when unburnt components are adsorbed or react on the catalyst within the protective layer to cause volume expansion, the protective layer hardly peels off from the solid-electrolyte body, and durability of the element is therefore increased. The spherically-protruded portion may be disposed on the measuring electrode or the surface of the solid electrolyte body.

The spherically-protruded portion is formed of an secured agglomeration of granulated particles, and may be formed by providing the granulated particles on the surface of the base portion of the solid-electrolyte body in a single layer or plural layers. The granule size of the granulated particles may be 40–100 $\mu$m, more preferably 50–80 $\mu$m. This is for forming wedge-like projections and recesses to provide a firm connection with the protective layer. If the granule size is less than 40 $\mu$m, the function as a wedge is not sufficiently provided. If the granule size exceeds 100 $\mu$m, adherence with the base portion becomes weak. Preferably, the spherically-protruded portion is distributed so as to leave recesses between granulated particles. This structure increases bonding strength with the protective layer, and also contributes to enlargement of the surface area of the electrode.

It is preferred that the material of the spherically-protruded portion is the same material as the base portion of the solid-electrolyte body, but any solid electrolyte may also be used. For example, the base portion may be made of $ZrO_2$—$Y_2O_3$ system and the spherically-protruded portion may be made of $ZrO_2$—(CaO, MgO) system, or the base portion may be made of $ZrO_2$—$Y_2O_3$ system and the spherically-protruded portion may be made of $ZrO_2$—$Y_2O_3$ system having a $Y_2O_3$ content different from that of the base portion.

The measuring electrode is coated with a porous first protective layer as described above, and the first protective layer is covered with a porous second protective layer (the configuration in the above-described 2nd Aspect).

The first protective layer is for preventing that the measuring electrode is subjected to volume expansion due to adsorption or reaction of unburnt components (CO and the like) of exhaust gases on the measuring electrode (made of noble metal) during use, and peels off from the solid-electrolyte body. The first protective layer may be constituted by ceramics, such as $Al_2O_3$, spinel, BeO, $ZrO_2$ and the like, or a mixture of these materials. A material comprised mainly of spinel is particularly preferred. Its porosity may be roughly 5–20%, and its thickness may be 100–180 $\mu m$, more preferably about 150 $\mu m$. As shown in FIG. 18, the thickness of the first protective layer at the distal end portion of the element may be larger (for example, 3/2–2 times) than the thickness at the rear portion (to be retained or mounted). This is for suppressing the generation of a phenomenon in which the output of the sensor becomes irregular when the sensor is used at low temperatures, that is, the so-called "chemical noise" phenomenon, thereby performing more accurate control even in applications at low temperatures. The length of the distal end portion in the axial direction may be selected from the range of 1/5–1/2 of the length in the axial direction from the distal end of the element to the mounting portion of the element. A different material may be used for a portion to be made thick.

As the noble-metal catalyst carried in the first protective layer for promoting oxidation of unburnt components in a gas to be measured, it is particularly preferred to use a material comprised mainly of platinum (Pt), for example, a material having not less than 80 wt % of Pt. Its carried amount may be within the range of 0.01–5 wt % relative to the entire amount of a material constituting the first protective layer. If the amount is less than 0.01 wt %, the effect does not appear. If the amount exceeds 5 wt %, there appears a possibility of producing clogging. However, it is preferred that the amount is not more than 1 wt % under the conditions of being exposed to concentrated (rich) exhaust gases. If the amount exceeds 1 wt %, unburnt components which exist in a large quantity is adsorbed on or react to the noble-metal catalyst, and cracks are produced in the protective layer. The catalyst may be uniformly or nonuniformly dispersed over the entire protective layer. The content of the noble metal may, for example, be larger at the distal end portion of the element where there are more unburnt components in the exhaust gas. Furthermore, the material of the catalyst may differ at each portion.

The second protective layer is constituted by a nonstoichiometric transition-metal oxide as described before. This is for preventing dispersion of the carried noble-metal catalyst in the first protective layer during application to cause a shift in $\lambda$-point (a point at which $\lambda=1$) and a decrease of the output. This constitution is also for further promoting the oxidation function of unburnt components of exhaust gases due to the catalytic action peculiar to the transition metal by the second protective layer itself and the action of the carried catalyst, and for preventing excessive adsorption of unburnt components on the carried catalyst by changing of electron holes in accordance with the amount of oxygen due to its nonstoichiometric property. As the transition-metal oxide, any oxide of a transition metal in subgroups 3A–7A and group 8 in the international periodic table may be selected as long as the above-described functions can be provided. However, an oxide of a transition metal in group 4A, for example titanium (Ti), or in group 8, for example, cobalt (Co) or nickel (Ni) is preferable. It is particularly preferred to use nonstoichiometric titanium suboxide represented by $TiO_2$ (x=not less than 1.8 and less than 2, more preferably not less than 1.95 and less than 2). This material can efficiently provide the above-described functions, and also is excellent in heat resistive property. The titanium suboxide may be not less than 50 wt %, more preferably not less than 70 wt %, relative to the total amount of the compositional material (exclusive of the carried catalyst) of the second protective layer. In this case, the residual material may be another nonstoichiometric transition-metal oxide, but it may also be constituted by a stoichiometric transition-metal oxide or the same ceramic material as the first protective layer. The porosity of the second protective layer may be larger than that of the first protective layer. This is for increasing passing property for the gas to be measured and for preventing the responsive property of the sensor. The porosity may, for example, be roughly 8% to 15–35% in volume. The pores may also exist as open pores (through pores).

Furthermore, from the same viewpoint, the thickness of the first protective layer may be thinner than that of the second protective layer. It may, for example, be 10 $\mu m$–50 $\mu m$.

The carried amount of the noble-metal catalyst in the second protective layer may also be smaller than that in the first layer, This is because the transition metal oxide also has a catalytic action. By reducing the carried amount, it is possible to prevent clogging due to the catalyst, and to intend effective utilization of the noble metal. Particularly, if the carried amount of noble metal is 0.02–5 mole % relative to the total amount of the second protective layer, the catalytic action can be effectively provided, and it is possible to prevent peeling of the layer caused by volume expansion according to the reaction between the catalyst and unburnt gases. The amount is, more preferably, 0.1–2 mole %. The catalyst may also be dispersed uniformly or nonuniformly over the entire second protective layer.

Even when at least a part (a specific portion) of the protective layer is formed of a nonstoichiometric transition-metal oxide (in the case of the above-described 4th or 5th aspect), that is, when the protective layer is not necessarily distinctly discriminated in two layers, the structure is preferably identical to that in the above-described second protective layer. The residual composition may also be identical to that of the above-described first protective layer. The entire protective layer may be also formed of a nonstoichiometric transition-metal oxide. The noble-metal catalyst may exist irrespective of the specific portion and the residual portion.

The production of the oxygen-sensor element will be generally outlined as follows.

The production may be performed by a method in which each component of the element is applied and formed stepwise. This approach is particularly preferred in the case of a closed-tube-like (test-tube-like) element. In this case, as the solid-electrolyte body, $Y_2O_3$ is added to and mixed with $ZrO_2$. The resultant mixture is calcined, pulverized, and formed (shaped). Subsequently, firing may be performed at a temperature between 1400°–1500° C. The sintering may be performed either under normal atmospheric pressure or pressurized atmosphere, or by pressure sintering like hot pressing. The formation of the electrodes may be performed by a normal plating processing, such as electrolytic plating, chemical plating and the like, as well as by a normal vapor phase deposition method, such as sputtering and vacuum deposition, or by screen printing. The protective layer may be formed by a method in which a solution or a powder of the material is applied by a brush, dipping, spraying and the like, and the subsequently fired, or by flame spraying. The carrying of the catalyst in the protective layer may be performed by dipping the body in a solution of a noble-metal salt and subsequently drying and firing the resultant body, or by using a paste-like substance provided by mixing a material for the protective layer and the noble-metal component.

Next, the preferred manners and functions with regard to the production method of the present invention, more particularly, to the processing steps for the side of another surface (the side on which the measuring electrode is to be formed) of the solid-electrolyte base material body, will be described.

A raw-material powder for the solid-electrolyte base material may be mixed and calcined, and then pulverized (not more than 2.5 μm). A secondary granular particles (20–150 μm) may then be formed by spray drying, and formed in a predetermined shape.

The spherically-protruded portion may be formed by applying spherical particles (or granules) having an average particle size of 50–100 μm on the surface of the solid-electrolyte base material, and then firing the resultant substance. This is for sufficiently leaving wedge-like projections and recesses even after electrode-deposition processing in a later step, to provide a strong connection with the first protective layer. That is, if the particle size of the spherical particles after firing is less than 40 μm, the function as a wedge can not satisfactorily be provided, and if the particle size exceeds 100 μm, adherence with the base portion becomes week. The particle (granule) size is, more preferably, 50–80 μm. Finer particles having a particle size of not more than 10 μm may also be mixed to further increase the strength. The solid-electrolyte base portion and the spherical particles may be subjected to cofiring. This is for increasing the adherence strength of the two materials. The firing temperature may be 1400°–1500° C. Furthermore, the spherical particles may be formed after performing electrolytic deposition processing. This is particularly effective when the measuring electrode can not be formed in a case where the spherical particles have previously been applied and formed. It becomes thereby possible to securely protect the measuring electrode, and to further increase bonding with the protective layer.

The electrode may be formed by a normal plating processing, such as electrolytic plating, chemical plating and the like, as well as a normal vapor-phase deposition method, such as sputtering and vacuum deposition, or by screen printing.

The first protective layer may be formed by various methods, such as a method in which a solution or a powder of the material is coated by a brush, applied by dipping, sprayed and the like, and then the resultant body is fired and the like, but plasma flame spraying is particularly preferred. The reason is that adherence strength between flame-sprayed particles is large, and it is possible to provide arbitrary porosity and pore size by properly changing the conditions of the plasma flame spraying.

The carrying the catalyst in the first protective layer may be performed by dipping the body in a solution of a noble-metal salt, and then drying and firing the resultant body. The concentration of the solution may be determined from the viewpoint that the catalyst is sufficiently dispersed and does not cause clogging during the dipping. For example, when the catalyst is Pt, as a solution in which Pt is sufficiently dispersed, there is a solution of $H_2PtCl_6$. The Pt concentration may be 0.01–5 g/l. If the Pt concentration is less than 0.01 g/l, the catalytic action becomes insufficient. If the Pt concentration exceeds 5 g/l, pores in the first protective layer are clogged, and the responsive property of the sensor becomes inferior. The dipping process may be performed with reducing pressure or pressurizing. The reason is that the solution of the noble-metal salt penetrates deeply into the first protective layer, and it is therefore possible to uniformly disperse the noble-metal catalyst within the first protective layer. The firing temperature may be 400°–700° C.

The second protective layer is formed by coating the first protective layer with a paste-like substance provided by mixing a material for the protective layer and the noble-metal component, and then firing the coated substance. The reason is that, by simultaneously performing the formation of the protective layer and the carrying of the catalyst, the catalyst is more firmly carried, to prevent dissipation during use and stably provide the catalytic action for a long period of time. Another reason is that, by providing the paste-like substance, a binder and the like are easily vaporized during firing, and it is possible to easily obtain desired porosity and pore size. The paste-like substance is obtained by mixing a binder, a solvent and the like as in the usual way. The coating method may be either coating by a brush, dipping, spraying or the like. However, plasma flame spraying is not suitable. The reason is that the sintering of the material of the protective layer proceeds during the flame spraying, and it is impossible to obtain pores in a desired state (especially in a state of high porosity). Mixing of the material of the protective layer and the catalyst to be carried may be performed by impregnating a powder of the protective-layer material with a solution of a noble-metal salt. This is for the purpose of uniform mixing. As the material of the protective layer, a compound which can form a transition metal oxide by pyrolysis, such as an hydroxide, a salt and the like, may also be used, besides the transition metal oxide. The particle size of the powder may be not more than 2 μm. The reason is that sinterability is thereby improved to increase adhesion strength, and hence the second protective layer becomes to hardly peel off during use. The particle size is, preferably 0.1–1.5 μm, and more preferably, 0.3–1.5 μm. Heat treatment may be performed at a temperature of 700°–900° C. in a nonoxidizing atmosphere.

7th Aspect

The heater is provided for heating the element, particularly at least a portion relating to the detection (measuring) function among its components. The heating is performed for exactly and stably maintaining the control of air-to-fuel ratio at low temperatures no higher than 400° C. The "portion relating to the detection function" indicates a portion which gives some influence on the generation of an electromotive force for the detection of an oxygen concentration of a gas to be measured The heater may be configured by a heating conductor (pattern) as a heating element and an insulator disposed at its surroundings. This configuration is for maintaining the insulating property from other components of the element. As the heating conductor, tungsten (W) and molybdenum (Mo) may mainly be used. In addition, metal components having high melting points, such as platinum (Pt), rhodium (Rh) and the like, may be used with being mixed with these constituents. Some oxides and the like may also exist to a degree such that not adversely influences the resistive property in the heating conductor. The heating conductor comprises a heating portion having a high resistive property and a terminal portion having a low resistive property used for the connection with power supply. The heating portion may be formed in a predetermined size and shape (for example, rectilinear or in a wavelike line) in accordance with the purpose for heating the sensor. As the insulator, $Al_2O_3$, spinel and the like are preferred. Especially preferred is a material which essentially consists of 89–99.7 wt % $Al_2O_3$, and contains 0.04–10 wt % $SiO_2$, 0.1–2 wt % MgO and 0.1–2.5 wt % CaO as sintering-aids. This material is preferred for protecting the heat-generating conductor even when exposed at a high temperature for a long period of time, and for stably maintaining the heating function. The heater may have various shapes, such as a rod, plate, tube and the like, in accordance with the location of the heater within the element and the shape of the element and the like. The thickness may also be properly selected.

The heater may be disposed so as to heat the electrode and each relevant component (the solid-electrolyte body and the like) of the element corresponding to the location of the electrode, since these components most influence the movement of oxygen ions, accordingly, the detection characteristics. For example, when the solid-electrolyte body is a test-tube-like body, a heater, particularly, rod-like heater, may be provided near the reference electrode in a space at the inner-surface side of the body. When the solid-electrolyte body is plate-like or tubular, the heater may be attached near the measuring electrode on the outer-surface side of the solid-electrolyte body. The heater may also be provided by being attached near the reference electrode on the inner-surface side of the solid-electrolyte body. In an element having a body (a tube-like body or the like) which has a space on the inner-surface side and the distal end of which is closed, and comprising each component (the solid-electrolyte body and the like) of the element on the outer-surface side of the body, a heater may be attached near the measuring electrode on the outer-surface side of the solid-electrolyte body. The heater may also be attached near the reference electrode on the inner-surface side of the solid-electrolyte body. In the element in which the heater is provided by being attached on the outer-surface side of the solid-electrolyte body, the heater is also coated with first and second protective layers as the measuring electrode.

The heater may be produced, for example, as in the following way. An $Al_2O_3$ base material is formed by press forming, extrusion and the like, and fired. A pattern of a heating element is formed on the surface of an $Al_2O_3$ green sheet. This formation is performed by plating, vapor-phase deposition (sputtering and the like), screen printing and the like. The side of the surface printed with the pattern is covered with another $Al_2O_3$ green sheet, and the pattern of the heating element covered with green sheets on both sides is connected to the $Al_2O_3$ base material. The unified body may be cofired. The firing temperature may be selected from the range of 1450°–1600° C. After the firing, terminal portions of the heating element are metallized, and leads from a power supply are connected thereto by brazing.

When the element has a body which has a space at the inner-surface side and the distal end of which is closed, the pattern may be formed by a laminated printing technique. This technique is particularly preferred in the case with a plate-like or tubular element. The laminated printing technique indicates a technique in which each component of the oxygen-sensor element is printed with being laminated on a predetermined green sheet (for example, a solid-electrolyte material), the printed green sheet is attached to a base material and fired to provide a unified body (for example, refer to JP Patent Kokai Publication No. 62-222159 (1987)). However, the outermost layer to be directly exposed to the gas to be measured may be separately formed by flame spraying, particularly plasma flame spraying. The reason is that the adhesion strength between flame-sprayed particles is strong, and hence the layer has excellent durability.

EXAMPLES

Embodiments of the present invention will be hereinafter explained with reference to the drawings.

EXAMPLE 1-1 (1ST ASPECT)

Figure 1:
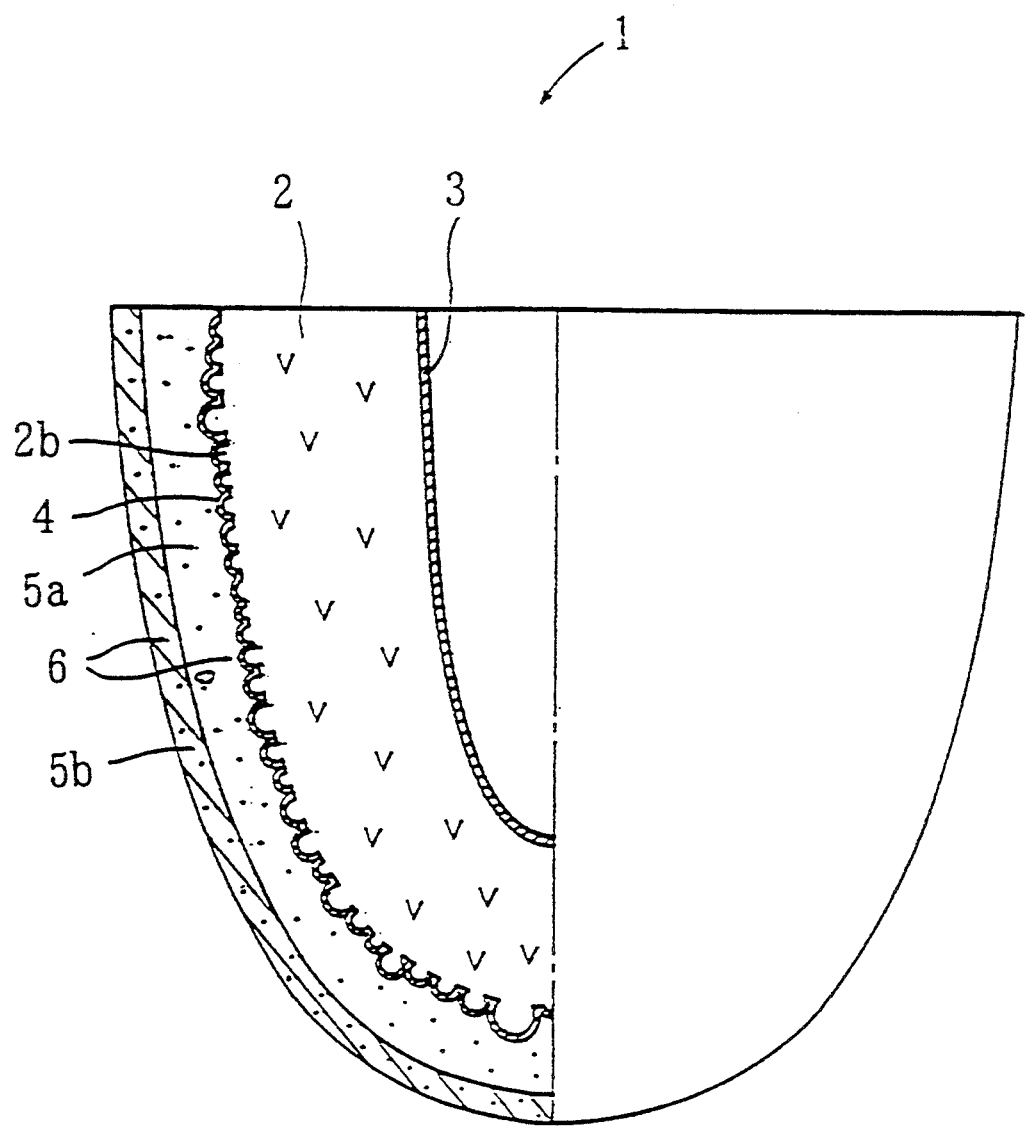
FIG. 1 is an explanatory diagram showing by partly breaking an oxygen sensor element used in an oxygen sensor of an embodiment.
Figure 2:
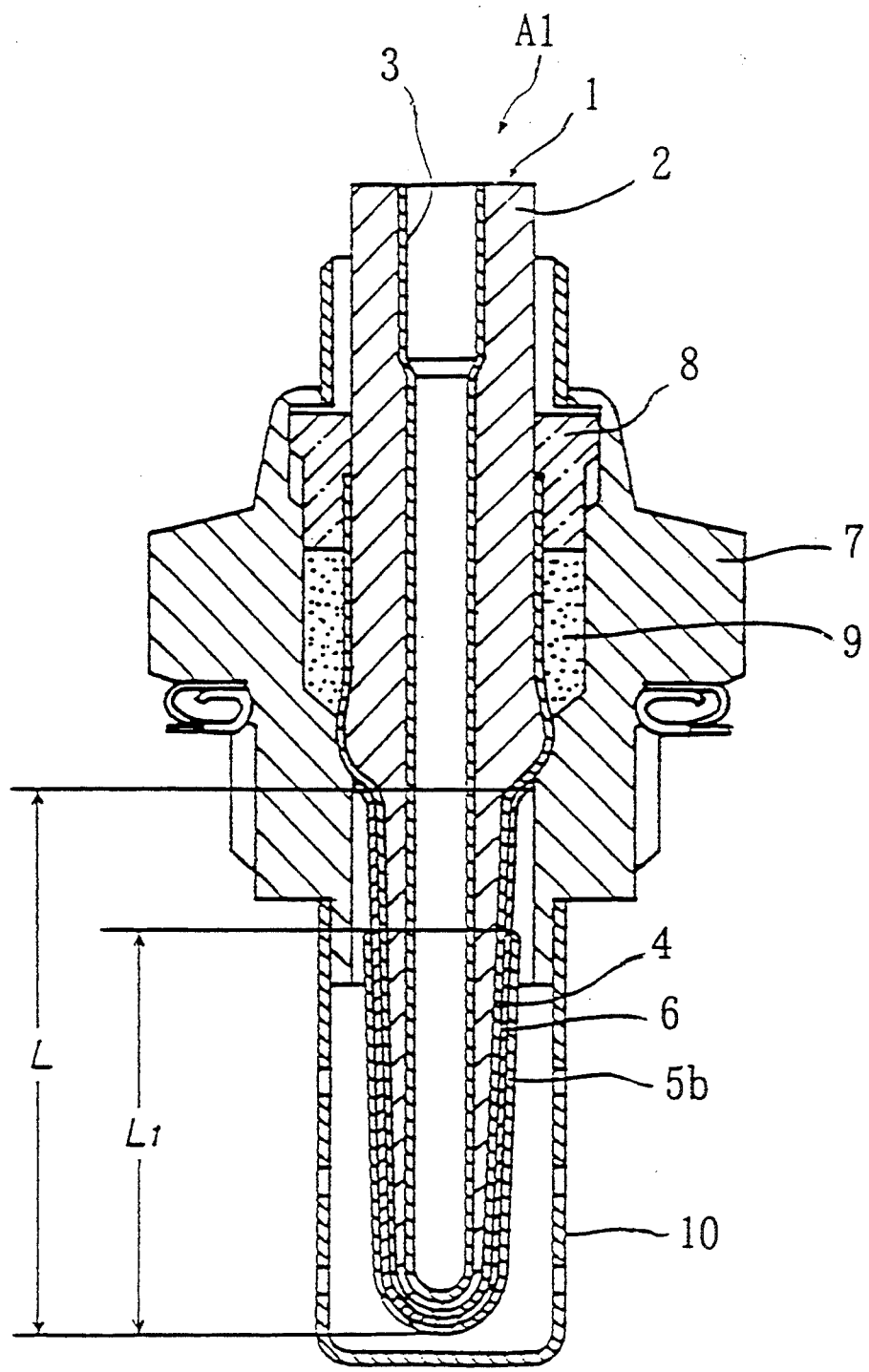
FIG. 2 is a cross-sectional view showing the entire configuration of the oxygen sensor.

FIG. 1 shows a distal end portion of a sensor element 1 used in an oxygen sensor A1. FIG. 2 shows the entire configuration of the oxygen sensor A1.

As shown in FIG. 1, the sensor element 1 formed in the shape of a hollow test tube is constituted by an oxygen-ion-conductive solid-electrolyte body 2 comprised mainly of stabilized or partially-stabilized zirconia. On the inner side (the reference-gas side) of the solid-electrolyte body 2, there is provided a platinum (Pt) electrode (a reference electrode) 3 having an excellent conductive-property and a catalytic action for a detection gas. On the other hand, on the outer side (the detection-gas side) of the solid-electrolyte body 2, there are secured large-grain spherical particles (protruded bodies) 2b consisting of stabilized or partially-stabilized zirconia having an average particle size of about 50 μm. Furthermore, on the surfaces of the spherical particles 2b, there is formed a Pt electrode (a measuring electrode) 4 identical to the above-described reference electrode 3.

On the surface of the measuring electrode 4, in order to prevent deterioration of the measuring electrode 4 due to the detection gas, there is provided a porous inner (first) protective layer 5a 100 μm thick having a granular texture, which is formed by spinel ($Al_2O_3$-MgO) carrying a Pt catalyst 6. At the outer surface of the inner protective layer 5a, there is provided a porous surface layer (a second protective layer) 5b 25 μm thick having a granular texture, which is formed by titanium suboxide ($TiO_x$) carrying the Pt catalyst 6. The average grain size of the $TiO_2$ grains forming the surface layer 5b is 0.3 μm, and the average pore size between the grains is 0.12 μm. Furthermore, as shown in FIG. 2, the surface layer 5b is formed centering around the distal end portion of the sensor element 1, and it is set so that the length L1 of the surface layer 5b is L1/L=3/5 relative to the length L of the detection-gas-side portion of the sensor element 1.

The sensor element 1 is fixed to a housing 7 made of stainless steel via an annular portion 8 and a filler powder 9. Furthermore, a protective tube 10 is covered at the distal end of the sensor element 1.

Next, the production method of the oxygen sensor A1 will be explained.

For forming the solid-electrolyte body 2 of the sensor element 1, 4 mole % yttria ($Y_2O_3$) having a purity of 99.9% is first added to a zirconia ($ZrO_2$) raw material having a purity of 99%, the added material is pulverized and mixed in wet state, and the resultant mixture is calcined at 1300° C. for 2 hours. The calcined material is then pulverized in wet state until 80% of particles have particles sizes of not more than 2.5 μm. A water-soluble binder is then added, and a material comprised of spherical secondary particles having a particle size of about 70 μm is prepared by spray drying and formed in a predetermined test-tube-like shape. Secondary particles having an average particle size of about 60–70 μm, which will become the spherical particles 2b, are then formed by another spray drying, and are coated by a brush on the outer surface of the solid-electrolyte body 2 to a thickness of about 100 μm. The coated body is then sintered at about 1500° C. for about 4 hours.

For further forming the reference electrode 3 and the measuring electrode 4 on both surfaces of the solid-electrolyte body 2, Pt, which has conductive property and catalytic action, is chemically plated on the surface of the solid-electrolyte body 2, and then subjected to heat treatment to be secured on the surface.

For forming the inner protective layer 5a, spinel is first coated on the surface of the measuring electrode 4 by plasma flame spraying, and the inner protective layer 5a is then dipped in platinic chloride ($H_2PtCl_6$) solution. Pt is further introduced into the inner protective layer 5a by evacuating, and the inner protective layer 5a is then dried.

For forming the surface layer 5b on the outer surface of the inner protective layer 5a thus formed, a titanium suboxide powder, which is a nonstoichiometric compound of the transition-metal oxide, is immersed in a $H_2PtCl_6$ solution having, for example, about 1 mole % Pt or Pt black, based on the metal element, relative to titanium suboxide, and then dried. Butyl carbitol and an organic binder is further added to provide a paste. The paste is coated on the outer surface of the inner protective layer 5a, and baked at about 700° C. in a nonoxidizing atmosphere. The surface layer 5b, which has a granular texture consisting of titanium suboxide particles and carries the Pt catalyst 6, is thereby formed.

Next, the effects of the oxygen sensor A1 of the present embodiment thus obtained will be explained.

In the oxygen sensor A1 of the present embodiment, the oxidation reaction of CO and HC in the detection gas is performed not only by the Pt catalyst 6, but also by titanium suboxide, the oxidation reaction can be surely performed, and adsorption of gas components on the Pt catalyst 6 is small. Hence, the sensor has an excellent responsive property. Accordingly, when feedback control of the air-to-fuel ratio is performed using the oxygen sensor A1 of the present embodiment, a shift in the control of air-to-fuel ratio is not produced. Moreover, since the carried amount of the Pt catalyst 6 is not less than 0.2 mole % and not more than 5 mole %, clogging due to the excess amount of the Pt catalyst 6 hardly occurs. In addition, since the amount of the Pt catalyst 6 is not too small, the decrease in the effect of the catalyst due to dissipation does not occur.

Furthermore, since the average grain size of the titanium suboxide grains constituting the granular texture of the surface layer 5b is 0.3 μm, it is possible to prevent that noxious materials, such as carbon and the like, pass through the surface layer 5b and reach the inner protective layer 5a. Accordingly, there never occurs that the carbon is converted into graphite and cracks and peeling are produced at the inner protective layer 5a and the surface layer 5b. Furthermore, since the grain size is not too small, there never occurs that the grains hinder the passing of the detection gas itself to reduce the responsive property of the sensor.

Furthermore, since the thickness of the surface layer 5b is 25 μm, it is possible to sufficiently prevent noxious materials such as Pb, and the responsive property of the sensor is not deteriorated either. In addition, since the surface layer 5b covers not less than 3/5 relative to the length of the protective layer 5a from the distal end of the sensor element 1, it is possible to sufficiently prevent deterioration of the performance of the oxygen sensor A1 due to noxious materials.

EXAMPLE 1-2

Next, an oxygen sensor A20 of another embodiment will be explained with reference to FIG. 3.

Figure 3:
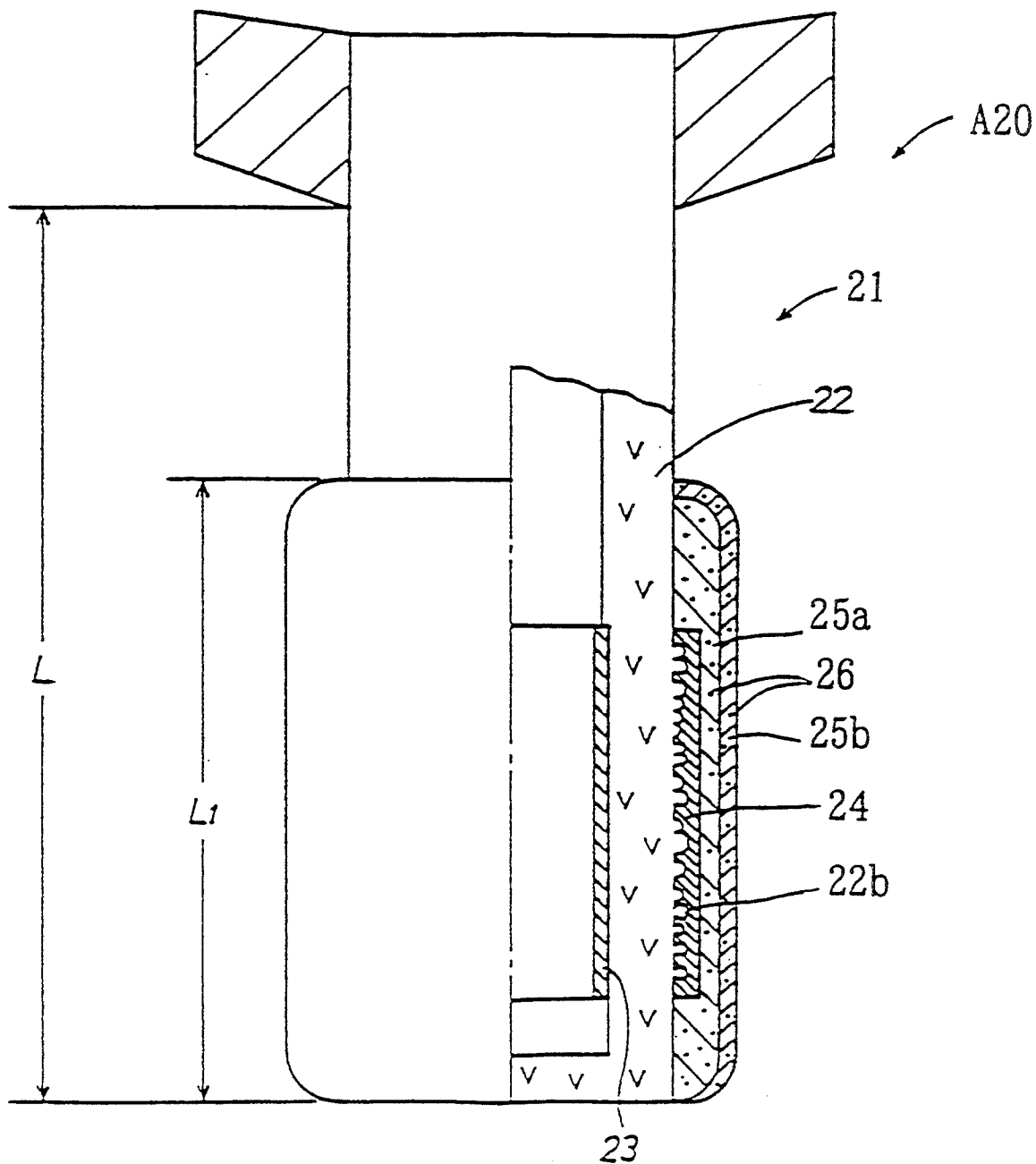
FIG. 3 is an explanatory diagram showing by partly breaking a part of the oxygen sensor of another embodiment.

The oxygen sensor A20 shown in FIG. 3 comprises a cylindrical sensor element 21 having a closed distal end. In FIG. 3, a Pt reference electrode 23 is formed on the inner circumferential surface on the reference-gas (usually atmospheric air) side of the solid-electrolyte body (base portion) 22 consisting of stabilized or partially-stabilized zirconia. On the other hand, at a lower portion of the outer circumferential surface on the detection-gas side of the solid-electrolyte body 22, spherical particles (protruded bodies) 22b consisting of stabilized or partially-stabilized zirconia having an average particle size of about 10 μm are secured. On the surface of the spherical particles 22b, there is further formed a Pt measuring electrode 24 identical to the above-described reference electrode 23.

On the surface of the measuring electrode 24, there is formed a porous inner protective layer 25a 70 μm thick, which consists of spinel carrying a Pt catalyst 26.

On the outer surface of the inner protective layer 25a, there is provided a porous surface layer 25b having a granular texture, which consists of titanium suboxide ($TiO_x$) carrying the Pt catalyst 26. The thickness of the surface layer 25b is 30 μm, and the average grain size of the granular texture is 0.3 μm. It is set so that the length L1 of the surface layer 25b is L1/L=3/5 relative to the length L of the portion of the sensor element 21 on the detection-gas side.

By such a configuration, in the present embodiment as well, the same effect as that in the above-described embodiment is provided. In addition, since the shape is cylindrical, there are the advantages that production is easy, and mounting to the housing is also simple.

Although, in the above-described embodiments, titanium suboxide is used as the nonstoichiometric compound of the transition metal oxide, CoO, NiO and the like may also be used as other materials.

Furthermore, as the carried catalysts 6 and 26, a noble metal including Pt may also be used other than only Pt. The noble metal including Pt is excellent in dispersibility in the surface layers 5b and 25b. Particularly, platinic chloride and nitric-acid-system platinum salts are suitable. When using platinic chloride, it is desirable to include not less than 90% of Pt.

For the above-described reference electrodes 3 and 23 and the measuring electrodes 4 and 24, Pt-Rh alloys, Rh and the like may, for example, be used other than Pt.

As a material for the inner protective layers 5a and 25a, alumina ($Al_2O_3$) and the like may, for example, be used other than spinel.

Furthermore, the provision of a heater at the above-described sensor elements 1 and 21 is suitable, since it is possible to improve operating characteristics of the oxygen sensor 1 at low temperatures (for example, no higher than 250° C.).

Next, explanation will be provided on data of experiments for the responsive property at the initial stage and after durability tests, which have been performed using the oxygen sensor A1 in the above-described embodiment, and observation of cracks, peeling and the like produced on the surface layer 5b and the like.

Experimental Data (1st aspect)

Figure 4:
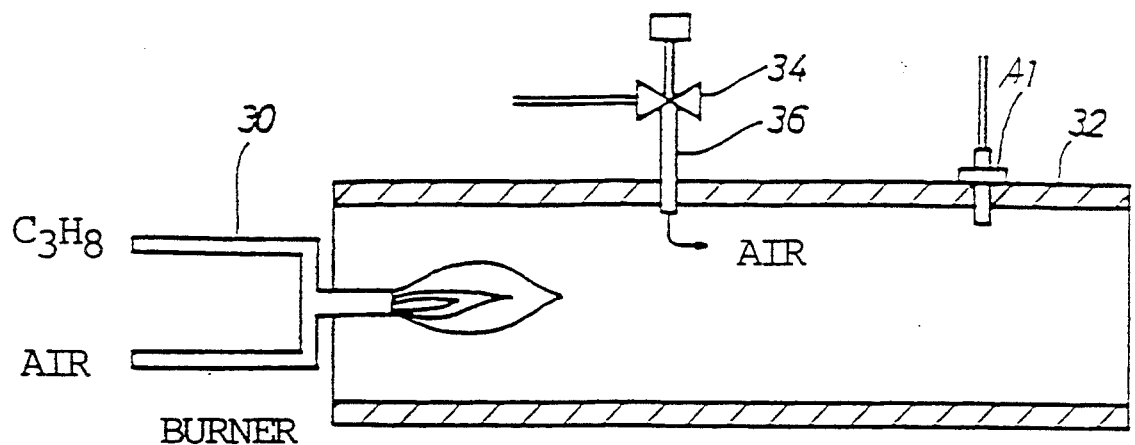
FIG 4 is a schematic configurational diagram showing a device for testing the performance of an oxygen sensor.

As shown in FIG. 4, an experimental device mixes propane ($C_3H_8$) and air with a weight ratio of $C_3H_8$:air=1:22 in a fuel-rich state, and burns the mixture within an exhaust pipe 32. An air inlet 36, which is opened and closed by a solenoid value 34, is provided in the midsection of the exhaust pipe 32, and introduction and the stop of introduction of air are performed. The oxygen sensor A1 is provided at a 30 cm downstream of the air inlet 36, and the arrangement is set so that the flow speed of the exhaust gas near the oxygen sensor A1 is 10 m/s.

In the oxygen sensor A1 used for the experiments, platinum was carried using 1 mole % or 5 mole % of $H_2PtCl_6$ as experimental examples, as shown in Table 1. Furthermore, various samples, in which conditions, such as the particle size of titania, the thickness of the surface layer 5b, the length ratio L1/L of the surface layer 5b, were changed, were produced and used.

Figure 5:
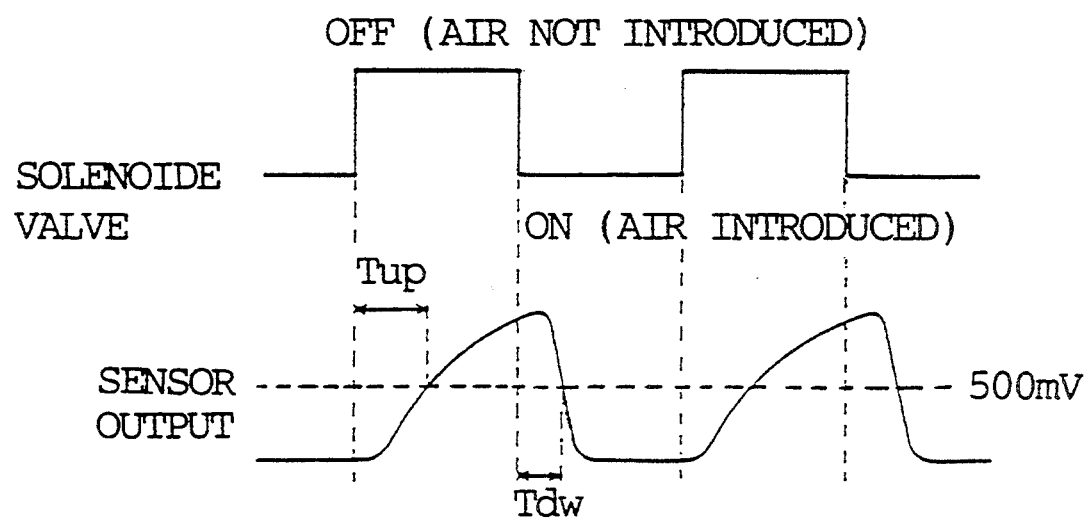
FIG. 5 is an explanatory diagram showing an output of an oxygen sensor.

As to the measuring method, as shown in FIG. 5, introduction or the stop of introduction of air was performed by switching on or off the solenoid valve 34, and rise response time Tup (ms) and fall response time Tdw (ms) until outputs of the oxygen sensor A1 become 500 mV, which is about one half of the maximum output, from switching time on and off of the solenoid valve 34, respectively, were measured.

Initial measurements of the rise response time Tup and the fall response time Tdw were first performed. Subsequently, as a durability test, after burning at the air-to-fuel ratio of 10 at a combustion temperature of 800°–850° C. for 200 hours, the rise response time Tup and the fall response time Tdw were measured again. In addition, the generation states of cracks and peeling of the surface layer 5b and the like were observed.

The results of these experiments and observations are shown in Table 1-1. In Table 1-1, Nos. 1–14 are data of experimental samples in which titania grains having an average grain sizes of 0.1–0.5 μm were used as the surface layer 5b, Nos. 15–18 are data of comparative samples in which grain sizes of titanium suboxide grains were outside of the above-described range, and No. 19 is data of a comparative sample in which the surface layer 5b was not provided.

As is apparent from those measurements and observations at the initial stage and after the durability tests, in experimental samples Nos. 1–14, both the rise response time Tup and the fall response time Tdw were small to indicate excellent responsive properties, and peeling and the like were not produced even after the durability tests. On the other hand, in comparative sample No. 15, the rise response time Tup and the fall response time Tdw after the durability test were large, and hence the sample is unsuitable. In comparative sample No. 16, the fall response time Tdw after the durability test was large, and hence the sample is unsuitable. In comparative sample No. 17, the initial rise response time Tup was large, and peeling was observed in a part of the surface layer 5b after the durability test. In comparative sample No. 18, peeling was observed in a part of the surface layer 5b. The responsive property of comparative sample No. 19 was excellent, since the sample did not carry the Pt catalyst 6. However, this sample is unsuitable, since it can not sufficiently perform oxidation reaction.

EXAMPLES (2ND–6TH ASPECTS)

Another embodiments of the present invention will be hereinafter explained.

Figure 6:
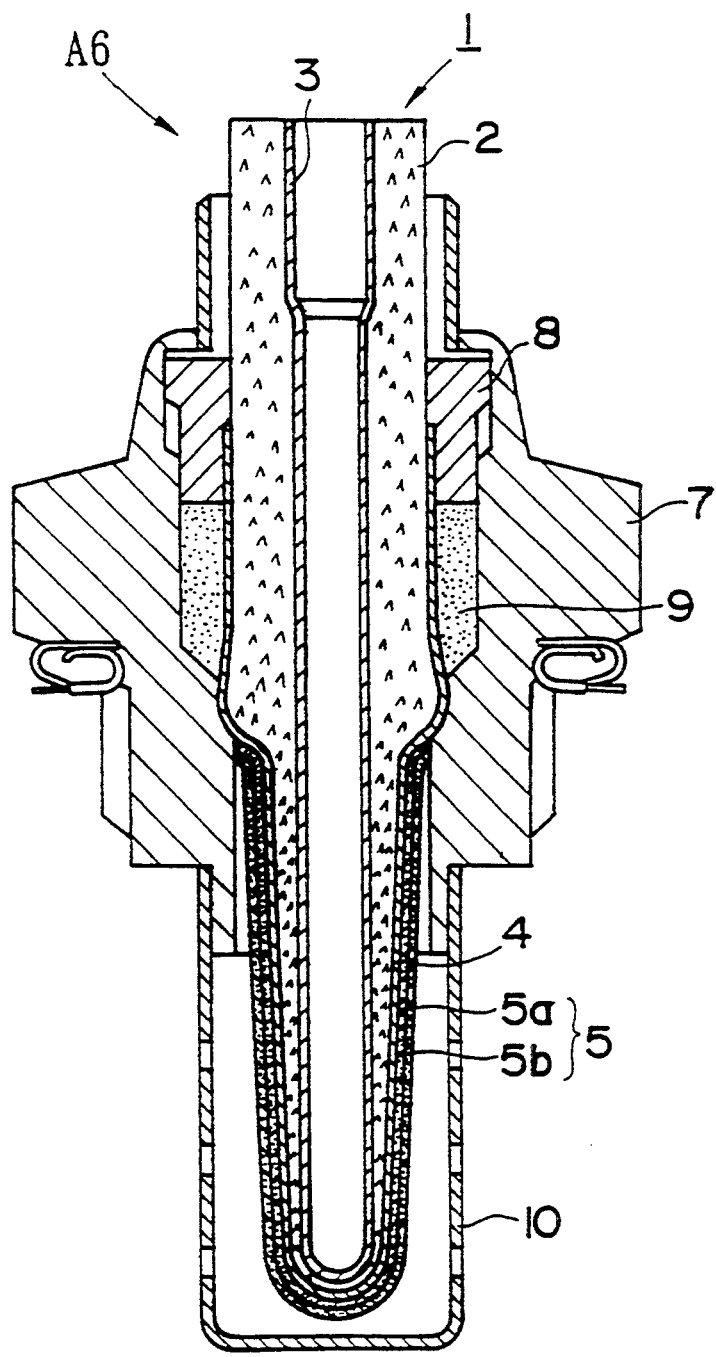
FIG. 6 is a cross-sectional view showing an embodiment of the oxygen-sensor element and the oxygen sensor of the present invention.
Figure 7:
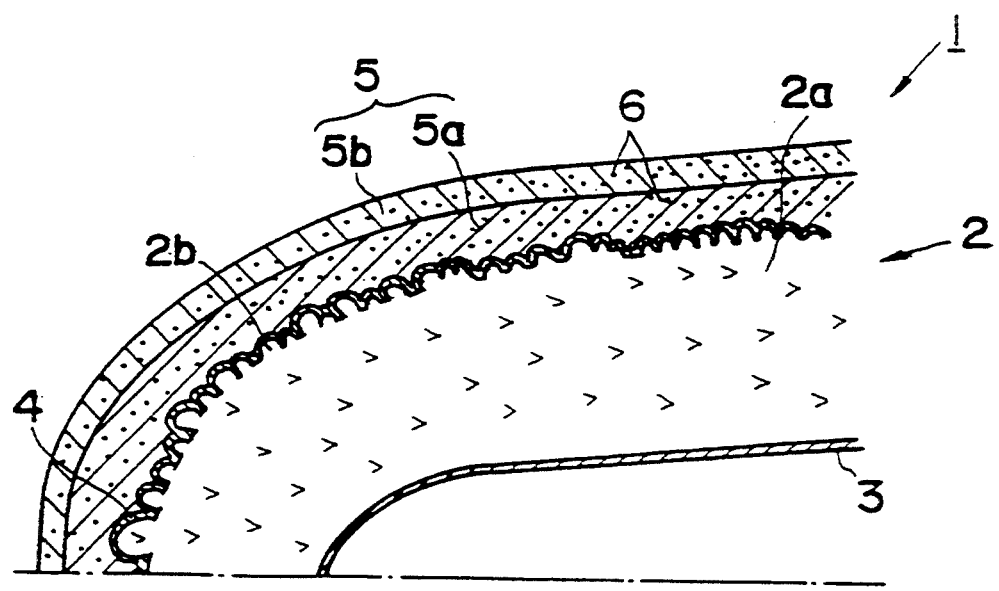
FIG. 7 is an enlarged partial cross-sectional view of FIG. 6.
Figure 8:
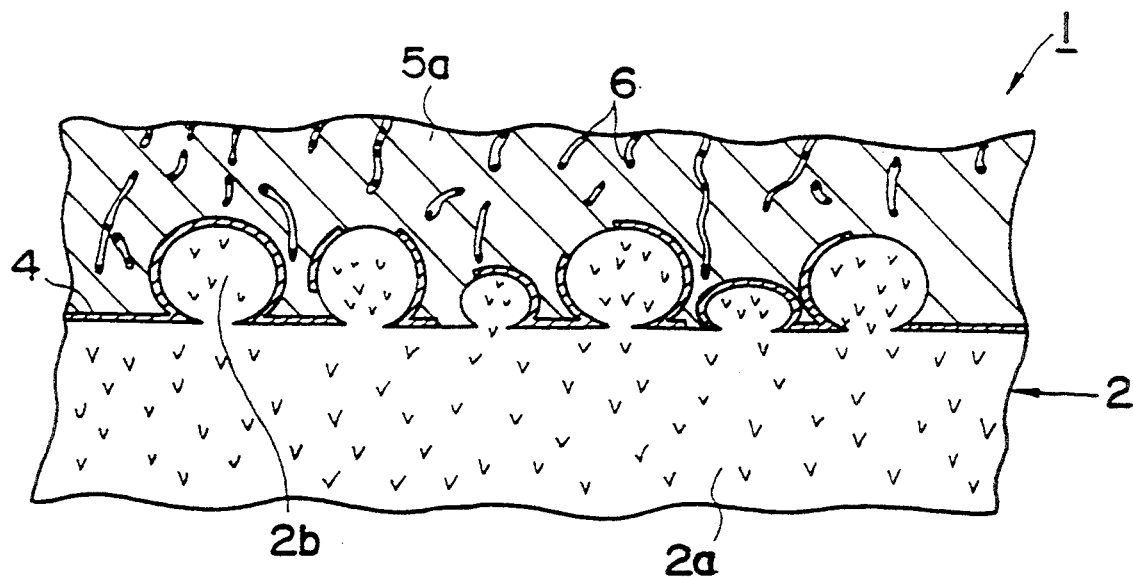
FIG. 8 is an enlarged partial cross-sectional view of FIG. 7.

FIGS. 6–8 show an oxygen sensor A6 as an embodiment of the present invention. In these figures an oxygen-sensor element 1 comprises in gross a solid-electrolyte body 2 capable of producing a difference in oxygen concentration by a reference gas and a gas to be measured (an exhaust gas), a pair of porous electrodes (an inner electrode) 3 and (an outer electrode) 4 formed on the inner and out surfaces of the solid-electrolyte body 2, a porous protective layer 5 covering the outer electrode 4, and a noble-metal catalyst 6 carried in the protective layer 5 by being uniformly dispersed. In this case, the solid-electrolyte body 2 is comprised of $ZrO_2$ to which $Y_2O_3$ is added, the electrodes 3 and 4 are both Pt electrodes, and the noble-metal catalyst 6 consists of Pt particles.

The solid-electrolyte 2 consists of a base portion 2a and spherically-protruded portion 2b disposed on its outer surface. Along the shape of spherically-protruded portion 2b, there are formed an outer electrode 4 and a protective layer 5. The protective layer 5 comprises a first protective layer 5a which is disposed on the relatively inner side and directly covers the outer electrode 4, and a second protective layer 5b which is disposed on the relatively outer side and is exposed to an exhaust gas. The protective layers 5a and 5b both carry the Pt catalyst 6. In this case, the first protective layer 5a consists of spinel, and the second protective layer 5b consists of titanium suboxide.

In FIG. 6, there are also shown a housing 6, a ring 8 for caulking, a filler 9, and a protective tube 10.

Figure 9:
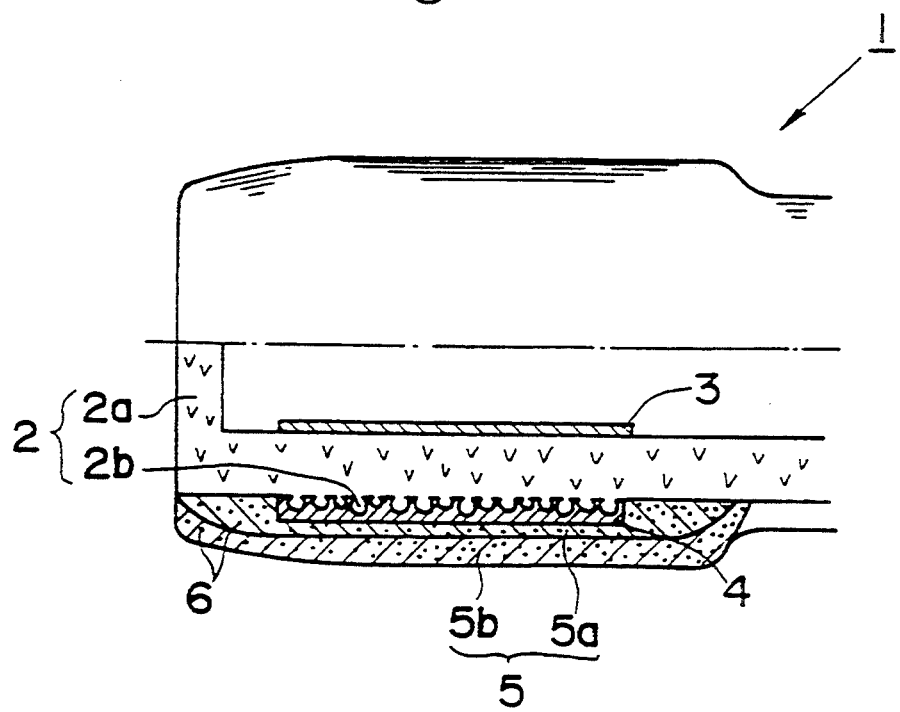
FIG. 9 is a partially cross-sectional view showing a further embodiment of the oxygen-sensor element of the present invention.

FIG. 9 shows another embodiment, that is, a plate-like oxygen-sensor element, in which another components are identical to those in the above-described embodiment. Hence, like components are indicated by like numerals, and the explanation thereof will be omitted.

Next, an example of production of the oxygen-sensor element of the present invention will be explained. The following steps are sequentially performed.

Step 1: 5 mole % $Y_2O_3$ having a purity of 99.9% is added to $ZrO_2$ having a purity of not less than 99% and mixed. The resultant mixture is calcined at 1300° C. for 2 hours.

Step 2: Water is added to the calcined material, and the material is pulverized in a ball mill in wet state until 80% of the particles have particle sizes of no larger than 2.5 μm.

Step 3: A water-soluble binder is added, and spherical granulated particles having an average particle size of 70 μm are then obtained by spray drying.

Step 4: The powder obtained at Step 3 is formed into a desired tubular shape (the shape of a test tube) by rubber pressing, and dried. The pressed body is then ground into a predetermined shape by a grinding tool.

Step 5: On the outer surface of the body, a sludge made by adding a water-soluble binder, cellulose, sodium glycolate and a solvent to the granulated particles obtained in Step 3 is applied.

Step 6: After drying, firing is performed at 1500° C. for 2 hours. The portion corresponding to the sensor element has a length in the axial direction of 25 mm, an outer diameter of about 5 mm$\phi$, and an inner diameter of about 3 mm$\phi$.

Step 7: A Pt layer 0.9 μm thick is deposited on the inner and outer surfaces by chemical plating, and the body is then fired at 1000° C.

Step 8: A $MgO.Al_2O_3$ (spinel) powder is coated by plasma flame spraying to form the first protective layer about 150 μm thick.

Step 9: The body is dipped in $H_2PtCl_6$ solution containing 0.05 g/l Pt, and is left for about 5 minutes in a reduced pressure by 50–100 mmHg.

Step 10: After drying, by coating a titanium suboxide paste including a noble-metal on the surface of the first protective layer and firing the coated body at 800° C. in a reducing atmosphere, the second protective layer about 25 μm thick having pores of about 2 μm is formed. The paste is obtained by dipping a titanium suboxide powder in $H_2PtCl_6$ solution or Pt black dispersoid, performing drying and impregnation with stirring, and then adding an organic binder and a solvent (butyl carbitol).

Furthermore, the oxygen sensor A6 is obtained by the following processes using the oxygen-sensor element 1 thus produced.

Step 11: After inserting the element 1 into the housing 7, the ring 8 for caulking and the filler 9, such as talc and the like, are inserted to secure the element 1 within the housing 7.

Step 12: The protective tube 10 is disposed covering the distal end of the element 1, and the distal end of the housing 7 and the rear portion of the protective tube 10 are welded together.

Step 13: Terminals and lead wires (not illustrated) are connected to the electrodes, and an outer tube (not illustrated) is covered to provide the oxygen sensor.

Experimental Data (2nd–6th aspects)

The following tests were performed for the oxygen-sensor elements of the present invention according to the above-described embodiment, and each evaluation item was investigated. The same investigation was performed for the comparative samples.

Tests 1 and 2

The oxygen-sensor elements prepared by changing the noble-metal catalyst source used in Step 10 and the carried amount of the catalyst in the second protective layer used in Process 10 were subjected to durability tests by a Bunsen burner. In test 1, the tip portion (the distal end portion) of each oxygen-sensor element was heated at 700°–850° C. in an incomplete combustion state in which air was hardly introduced. In test 2, the tip portion was heated at about 850° C. in a nearly complete combustion state in which air was introduced. The test samples endured 500 hours in both durability tests.

Evaluation Item A:

The oxygen sensor equipped with the oxygen-sensor element after the above-described testing was mounted to a combustion tube (the inner diameter is 43 mm), a burner flame was blown from a portion 1 m apart, and the responsive property of the sensor was evaluated.

Evaluation Item B:

Similarly, the oxygen sensor after the testing was mounted at a predetermined position in an engine of an actual car, control by the sensor was performed, λ-scanning value (the average value of the controlled air-to-fuel ratio) disposed at more downstream position, and λ-characteristic was evaluated.

Evaluation Item C:

The state of the surface portion of the element was evaluated by visual inspection.

The results of these evaluations are shown in Table 2-1.

As is apparent from Table 2-1, the oxygen-sensor elements (and the oxygen sensors) according to the embodiment show excellent results with regard to evaluation items A, B and C for tests 1 and 2 compared with the comparative samples. It is also possible to recognize that the carried amount of the catalyst in the second protective layer is preferred to be less than 8.0 mole %.

Test 3

Using the oxygen-sensor elements in which the carried amount of each catalyst in the first and second protective layers was changed, frequency (Hz) while performing control by the sensor was measured as its initial characteristic (before durability test) [evaluation item D].

The oxygen sensor in the above-described elements were mounted at a predetermined position in the engine of an actual car, durability test was then performed at an A/F (air-to-fuel ratio) 10 (a rich atmosphere) at an exhaust-gas temperature of 700° C. for 200 hours, and the above-described evaluation items B and C were also investigated.

From Table 2-2 as well, the excellent results of the present embodiment are proved. It is also possible to recognize that, under a condition in which the element is exposed to such a concentrated (rich) exhaust gas, the carried amount of the catalyst in the first protective layer is preferred to be less than 1 wt %.

EXAMPLE (7TH ASPECT)

An embodiment according to the 7th aspect of the present invention will be hereinafter explained.

Figure 10:
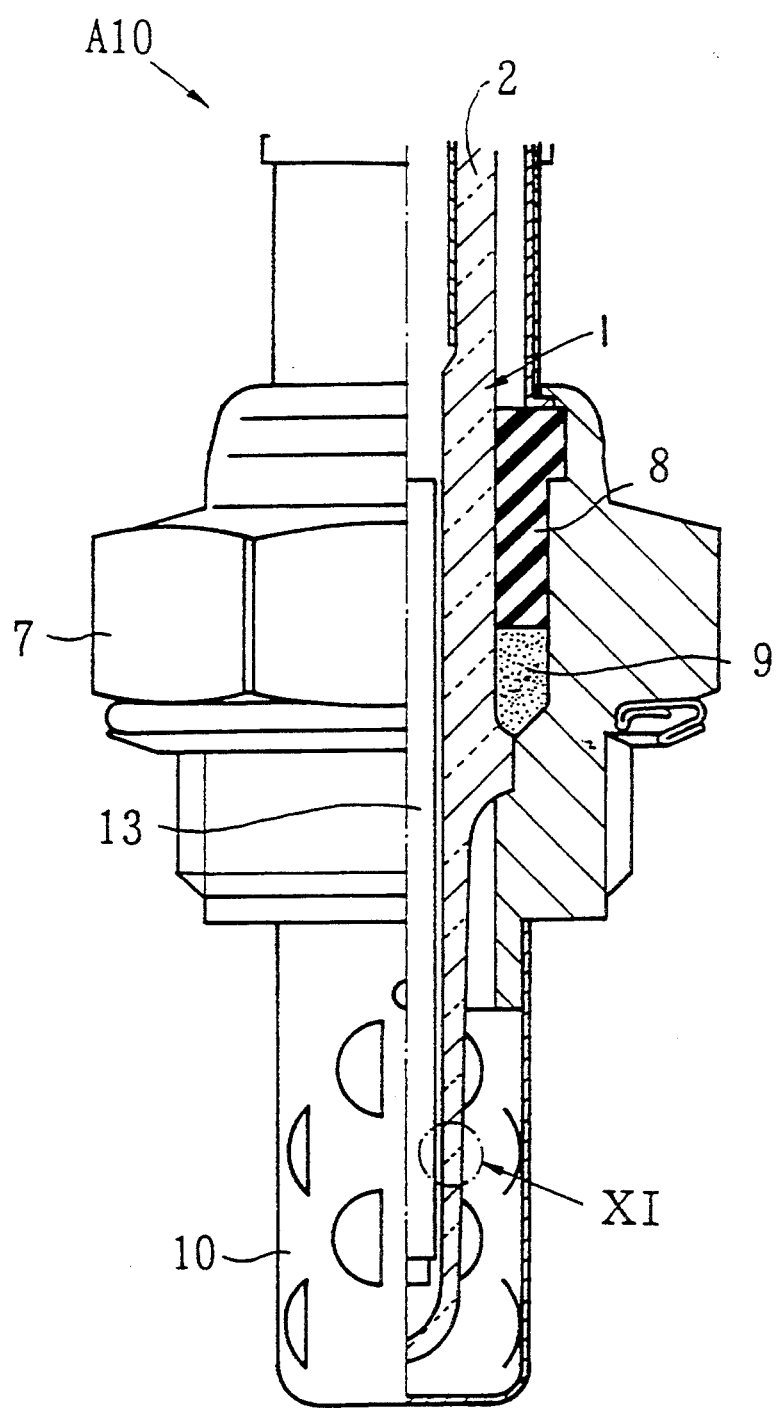
FIG. 10 is a cross-sectional view showing a still further embodiment of the oxygen-sensor element and the oxygen sensor of the present invention.
Figure 11:
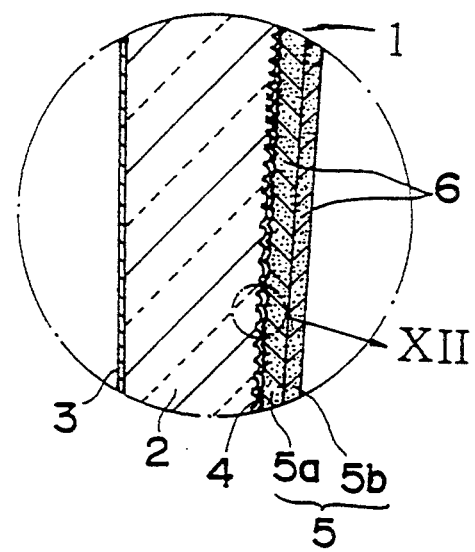
FIG. 11 is an enlarged cross-sectional view of portion XI in FIG. 10.
Figure 12:
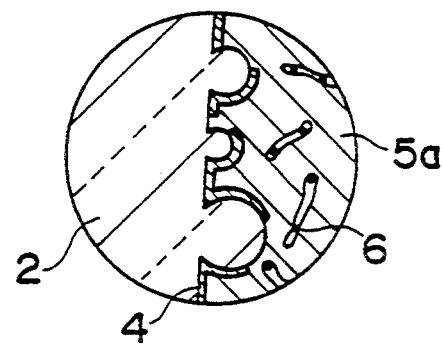
FIG. 12 is an enlarged cross-sectional view of portion XII in FIG. 11.

FIGS. 10–12 show an oxygen sensor A10 of the present embodiment. In these figures, an oxygen-sensor element 1 comprises in gross a solid-electrolyte body 2 capable of producing difference in oxygen concentration by a reference gas and a gas to be measured (an exhaust gas), a pair of porous electrodes (an inner electrode) 3 and (an outer electrode) 4 formed on the inner and outer surfaces of the solid-electrolyte body 2, a porous protective layer 5 covering the outer electrode 4, and a noble-metal catalyst 6 carried in the protective layer 5 by being uniformly dispersed. In this case, the solid-electrolyte body 2 consists of $ZrO_2$ to which $Y_2O_3$ is added, the electrodes 3 and 4 are both Pt electrodes, and the noble-metal catalyst 6 consists of Pt particles.

The solid-electrolyte 2 consists of a base portion 2a and spherically-protruded portion 2b situated on its outer surface. Along the shape of the spherically-protruded portion 2b, there are formed the outer electrode 4 and the protective layer 5. The protective layer 5 consists of a first protective layer 5a which is disposed on the relatively inner side and directly covers the outer electrode 4, and a second protective layer 5b which is disposed on the relatively outer side and is exposed to an exhaust gas. The protective layers 5a and 5b both carry the Pt catalyst 6. In this case, the first protective layer 5a consists of spinel, and the second protective layer 5b consists of titanium suboxide. A heater (a heating conductor) 13 is provided as a rod-like body extending along the central axis of the element 1. Accordingly, as for portions which relate to the detection function among the components of the element, the inner electrode 3, the solid-electrolyte body, the outer electrode 4, the first protective layer 5a, and the second protective layer 5b are heated in the order starting from the inner side.

Figure 18:
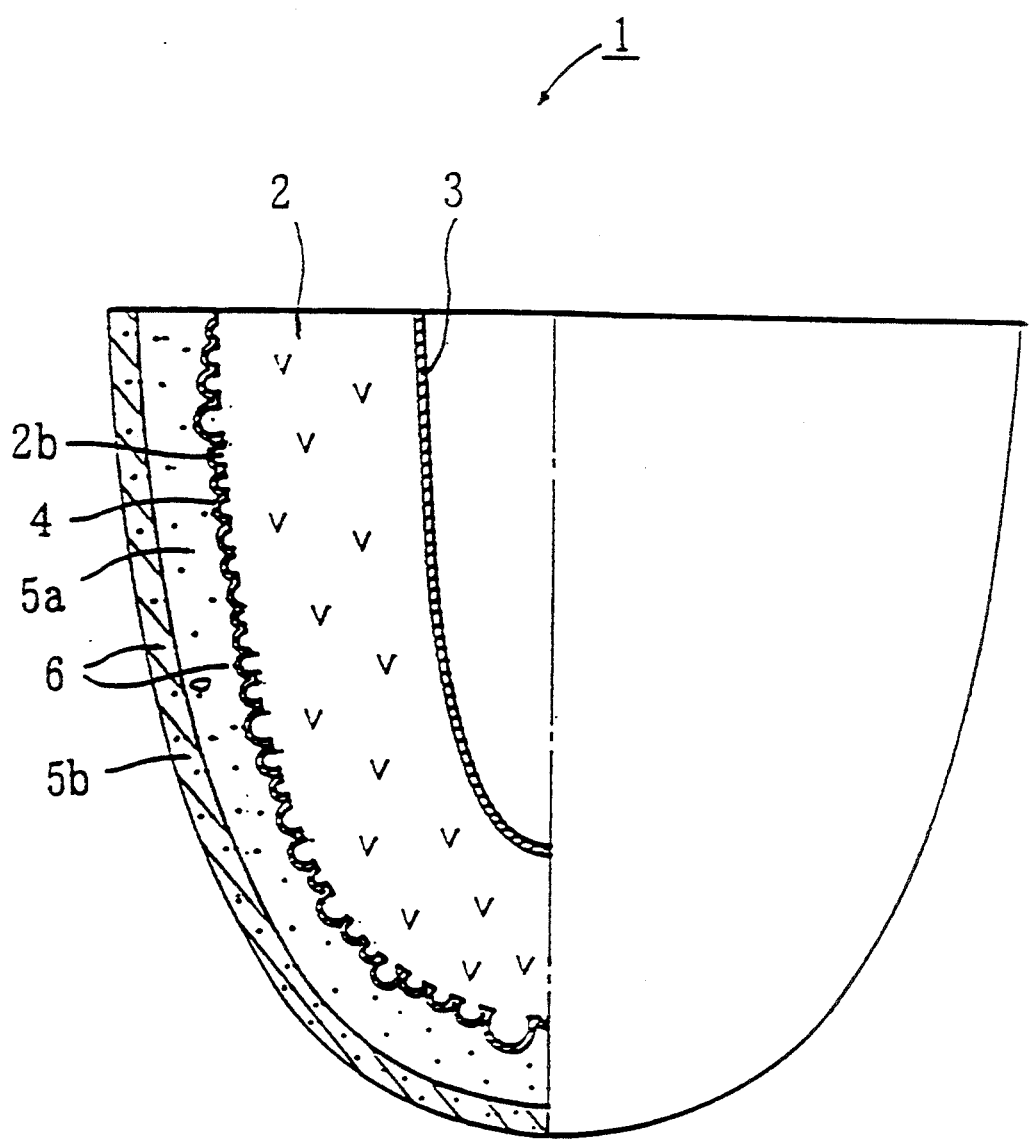
FIG. 18 is a front view, partially broken away, of an oxygen sensor according to yet another embodiment of the invention.

In FIG. 10, there are also shown a housing 7, a ring 8 for caulking, a filler 9, and a protective tube 10. In FIG. 18, there is shown an insulating layer 12.

Figure 13:
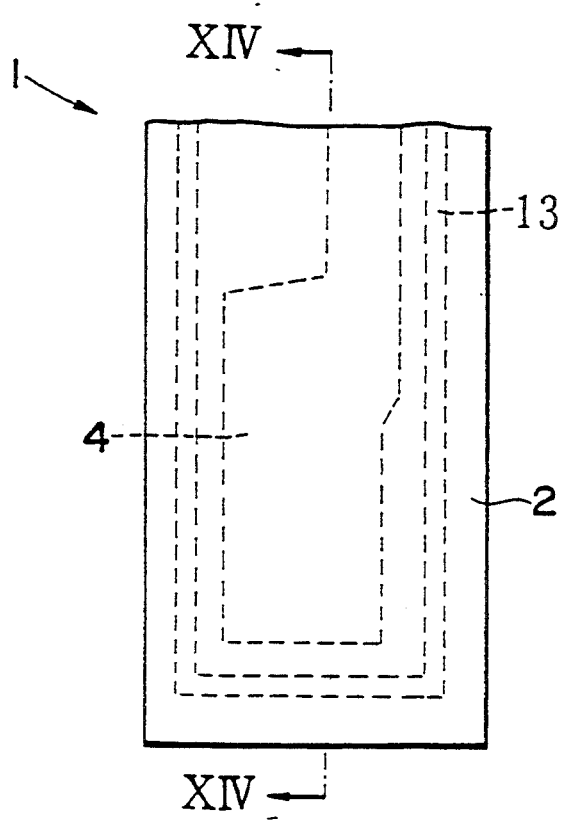
FIG. 13 is a plan view showing still further embodiment of the oxygen-sensor element of the present invention.
Figure 14:
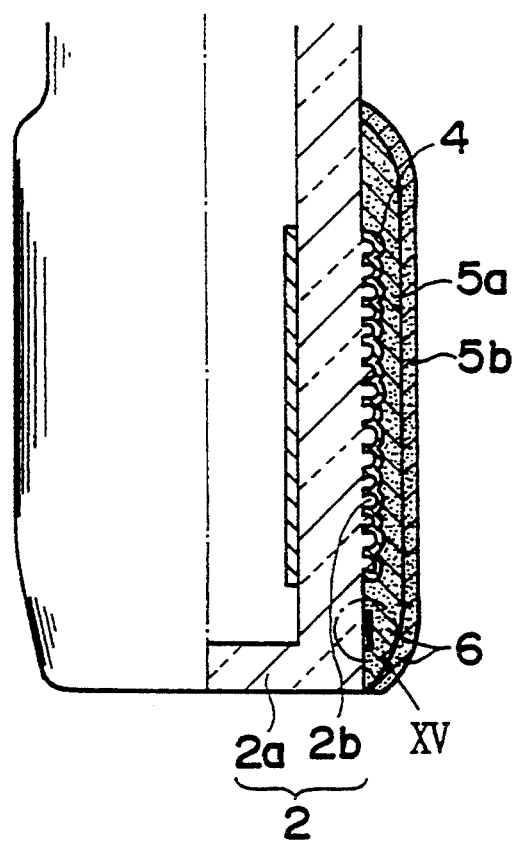
FIG. 14 is a cross-sectional view taken on line XIV–XIV in FIG. 13.
Figure 15:
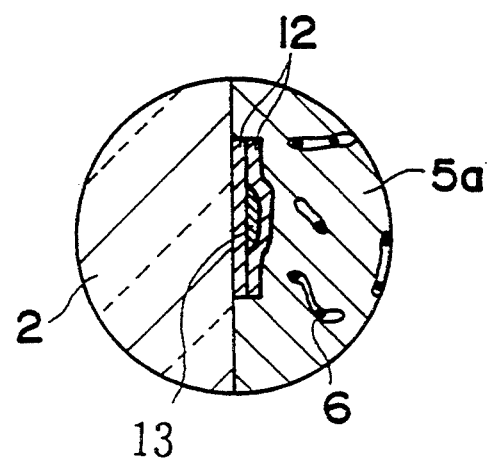
FIG. 15 is an enlarged cross-sectional view of portion XV in FIG. 14.

FIG. 13 shows another embodiment, that is, a plate-like oxygen-sensor element. In the present embodiment, the heater 13 is disposed by being applied in a generally U-like shape with maintaining a constant separated distance from the outer electrode 4 on the outer-surface side of the solid-electrolyte body 2. Accordingly, particularly as for potions which relate to the detection function among the components of the element, the outer electrode 4, and the solid-electrolyte body 2 and the inner electrode 3, which are disposed on the inner side, and the first and second protective layers 5a and 5b, which are disposed on the outer side, are heated. Since other components are almost identical to those in the above-described embodiment, like components are indicated by like numerals, and the explanation thereof will be omitted.

Next, an example of the production of the oxygen-sensor element of the present aspect will be explained. The following steps are sequentially performed.

(1) Production of the Main Body of the Element

Step 1: 5 mole % $Y_2O_3$ having a purity of 99.9% is added to $ZrO_2$ having a purity of not less than 99% and mixed. The resultant mixture is calcined at 1300° C. for 2 hours.

Step 2: Water is added to the calcined material, and the material is pulverized in a ball mill in wet state until 80% of the particles has particle sizes of no larger than 2.5 μm.

Step 3: A water-soluble binder is added, and spherical granulated particles having an average particle (granule) sizes of 70 μm are then obtained by spray drying.

Step 4: The powder obtained at Step 3 is formed into a desired tubular shape (the shape of a test tube) by rubber pressing, and dried. The pressed body is then ground into a predetermined shape by a grinding tool.

Step 5: On the outer surface of the body, a sludge made by adding a water-soluble binder, cellulose, sodium glycolate and a solvent to the granulated particles obtained in Step 3 is applied.

Step 6: After drying, firing is performed at 1500° C. for 2 hours. The portion corresponding to the sensor element has a length in the axial direction of 25 mm, a outer diameter of about 5 mmφ, and an inner diameter of about 3 mmφ.

Step 7: A Pt layer 0.9 μm thick is deposited on the inner and outer surfaces by chemical plating, and the body is then fired at 1000° C.

Step 8: A $MgO \cdot Al_2O_3$ (spinel) powder is coated by plasma flame spraying to form the first protective layer about 150 μm thick.

Step 9: The body is dipped into $H_2PtCl_6$ solution containing 0.05 g/l Pt, and is left for about 5 minutes in a reduced pressure by 50–100 mmHg.

Step 10: After drying, by coating a titanium suboxide paste including a noble-metal on the surface of the first protective layer and firing the coated body at 800° C. in a reducing atmosphere, the second protective layer about 25 μm thick having pores of about 2 μm is formed. The paste is obtained by dipping a titania powder in $H_2PtCl_6$ solution or Pt black dispersoid, performing drying and impregnation with stirring, and then adding an organic binder and a solvent (butyl carbitol).

(2) Production of the Heater

Step 1: An $Al_2O_3$ composite, which consists mainly of an $Al_2O_3$ powder and includes a powder of a sintering aid, is subjected to wet blending in a ball mill, and then dehydrated and dried.

Step 2: A binder is added to a base which consists of the material in Step 1, and the resultant mixture is extruded in the form of a pipe. The extruded material is subjected to heat treatment at 800° C. to provide a base material.

Step 3: The material in Step 1 is made into a slurry, and a first green sheet 0.8 mm thick is formed by a taping method.

Step 4: A pattern of a heating element is coated by screen printing on the surface of the first green sheet using a Pt paste which is prepared by mixing Pt black and platinum sponge at a ratio of 2:1.

Step 5: A second green sheet 0.3 mm thick, formed in the same way as the first green sheet, is pressed on the surface printed with the pattern covering the pattern.

Step 6: A paste-like substance is coated on the surface of the second green sheet of the laminated sheet obtained. The coated sheet is wound around the base material in Step 2 so that the coated surface contacts the base material, and then pressed. After removing resin, the resultant material is fired at 1550° C.

Step 7: Terminal regions of the body obtained is subjected to Ni plating, and the plated terminal regions are connected to terminals for guiding lead wires using Ag brazing material.

(3) Production of the Oxygen Sensor

Using the oxygen-sensor element 1 thus produced, the oxygen sensor A 10 is obtained by the following processes.

Step 1: After inserting the element 1 into the housing 7, the ring 8 for caulking and the filler 9, such as talc and the like, are charged to secure the element 1 within the housing 7.

Step 2: The heater 13 is inserted into the element 1.

Step 3: Leads are connected to the electrodes 3 and 4 via the terminals, and leads are also connected to the heater 7.

Step 4: The protective tube 10 is disposed covering the distal end portion of the element 1, and the distal end of the housing 7 and the rear end of the protective tube 10 are welded together.

Step 5: The outer tube is covered to provide the oxygen sensor.

Test Examples (7th aspect)

The following tests were performed for the oxygen-sensor element (a) of the present aspect according to the above-described embodiment, and each evaluation item was investigated. Furthermore, for the purpose of comparison, (b) an element without a heater (other components are identical to those in the embodiment), (c) a conventional commercially available sensor element (a product of NGK Spark Plug Co., Ltd) without a heater as a comparative sample, and (d) an element identical to that in (c), but with a heater, were adopted.

The oxygen sensor was mounted at a predetermined position in the engine of an actual car, control by the sensor was performed, λ-scanning value (the average value of controlled air-to-fuel ratio) at more downstream position was investigated, and λ-characteristic was evaluated. The investigation was performed for the following two kinds of cars.

(1) A first car in which the tip temperature of the element becomes not less than 450° C. at a constant-speed driving of 80 km/hr, and a relatively rich control is performed.

(2) A second car in which the tip temperature of the element rises only up to 400° C. at most at a constant speed-driving of 80 km/hr, and a relatively lean control is performed.

Figure 16:
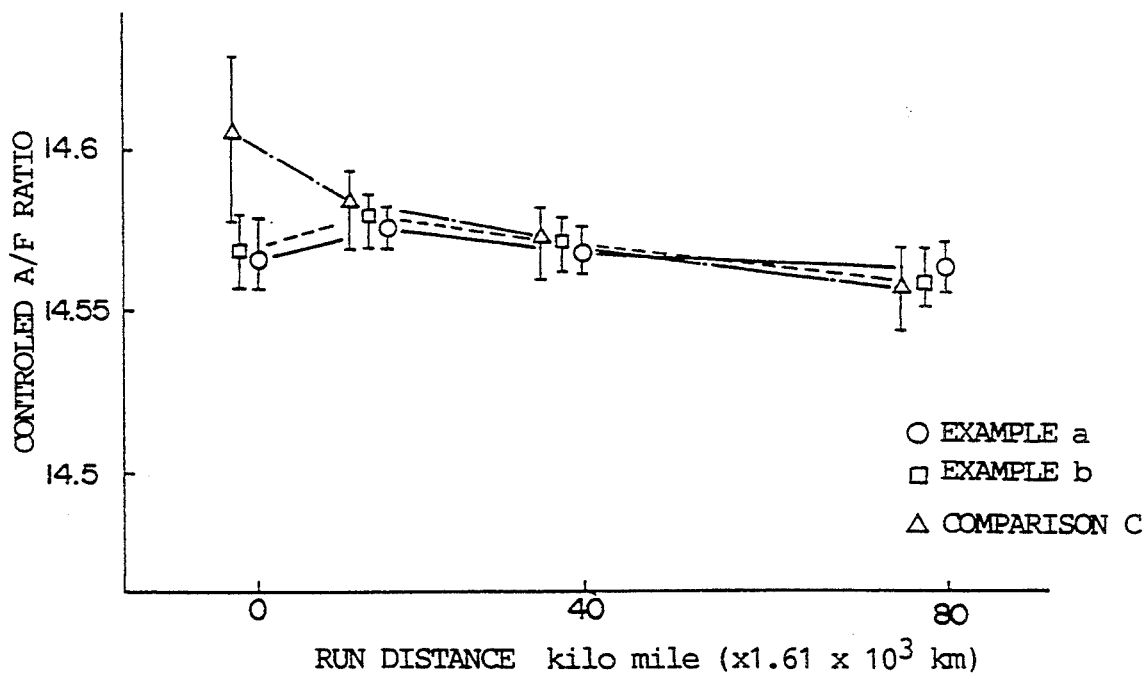
FIGS. 16 and 17 are graphs showing the results of test example, and represent results relating to first and second vehicles, respectively.
Figure 17:
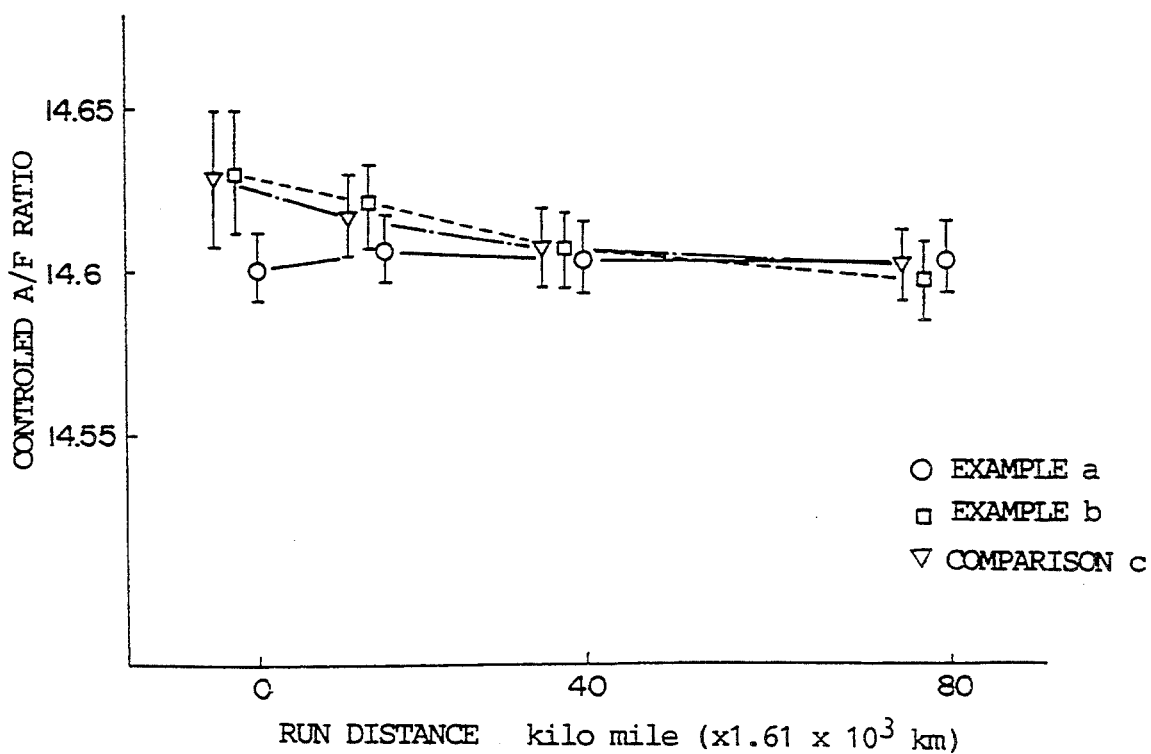

The results are shown in FIGS. 16 and 17, respectively.

As is evident from FIG. 16, in the first car, the element (a) according to the present invention has smaller variations and change in the lapse of time for the air-to-fuel ratio, and shows values at somewhat rich side compared with the element (c). Hence, it is possible to reduce initial $NO_x$. The element (a) can also maintain a control identical to that at the initial state even after the durability test. The element (b) also shows excellent results in the first car.

Furthermore, as is evident from FIG. 17, in the second car as well, the element (a) according to the present invention has smaller variations and change in the lapse of time for the air-to-fuel ratio, and also shows values at somewhat rich side compared with the elements (b) and (d) for comparison. Accordingly, it is possible to reduce initial $NO_x$ even at low temperatures, and to suppress variations in emission. On the other hand, the element (b) produces variations in the air-to-fuel ratio as the element (d) under such conditions.

TABLE 1-1

| Samples No. | Used amount of $H_2PtCl_6$ [mole % Pt] | Particle size of $TiO_2$ [μm] | Thickness of surface layer [μm] | Ratio of length of surface layer L1/L | Initial measurement | | Measurment after durability test for 200 hrs | | Suita-bility** | Results of observation |
|---|---|---|---|---|---|---|---|---|---|---|
| | | | | | Tup [ms] | Tdw [ms] | Tup [ms] | Tdw [ms] | | |
| 1 | 0.2 | 0.3 | 25 | 2/3 | 91 | 61 | 94 | 65 | ○ | No abnormality |
| 2 | 1 | 0.1 | ↑ | ↑ | 96 | 65 | 99 | 68 | ○ | |
| 3 | ↑ | ↑ | ↑ | ↑ | 93 | 63 | 96 | 64 | ○ | |
| 4 | ↑ | 0.2 | 50 | ↑ | 95 | 64 | 98 | 67 | ○ | |
| 5 | ↑ | 0.3 | 5 | ↑ | 91 | 70 | 93 | 70 | ○ | |
| 6 | ↑ | ↑ | 10 | ↑ | 91 | 63 | 96 | 65 | ○ | |
| 7 | ↑ | ↑ | 25 | 4/5 | 94 | 64 | 97 | 65 | ○ | |

TABLE 1-1-continued

| Samples No. | Used amount of $H_2PtCl_6$ [mole % Pt] | Particle size of $TiO_2$ [μm] | Thickness of surface layer [μm] | Ratio of length of surface layer L1/L | Initial measurement Tup [ms] | Initial measurement Tdw [ms] | Measurment after durability test for 200 hrs Tup [ms] | Measurment after durability test for 200 hrs Tdw [ms] | Suitability** | Results of observation |
|---|---|---|---|---|---|---|---|---|---|---|
| 8 | 1 | ↑ | ↑ | 2/3 | 92 | 61 | 96 | 63 | ◯ | |
| 9 | ↑ | ↑ | 50 | ↑ | 94 | 65 | 98 | 66 | ◯ | |
| 10 | ↑ | 0.5 | 25 | ↑ | 92 | 59 | 97 | 62 | ◯ | |
| 11 | 5 | 0.3 | 30 | 3/5 | 93 | 64 | 97 | 66 | ◯ | |
| 12 | ↑ | ↑ | 60 | ↑ | 99 | 70 | 102 | 66 | ◯ | |
| 13 | ↑ | 0.5 | 30 | ↑ | 92 | 63 | 95 | 65 | ◯ | |
| 14 | ↑ | ↑ | 50 | ↑ | 94 | 69 | 98 | 65 | ◯ | |
| *15 | 1 | 0.05 | 30 | 2/3 | 99 | 67 | 104 | 71 | X | Tup and Tdw unsuitable after durability test |
| *16 | ↑ | 0.7 | 25 | ↑ | 93 | 63 | 96 | 71 | X | Tdw unsuitable after durability test |
| *17 | ↑ | ↑ | 75 | ↑ | 100 | 69 | 96 | 70 | X | Initial Tup unsuitable |
| *18 | ↑ | 1.0 | 50 | ↑ | 93 | 62 | 97 | 66 | X | Surface layer peeled off after durability test |
| *19 | X | X | X | X | 90 | 80 | 96 | 75 | X | |

*Comparative Samples
**◯: Suitable
X: Unsuitable

TABLE 2-1

| Sample No. | Existence of steps | Catalyst source used in Step 10 | Carried amount of catalyst in 2nd protective layer (mole %) | Test 1 Item A | Test 1 Item B | Test 1 Item C | Test 2 Item A | Test 2 Item B | Test 2 Item C |
|---|---|---|---|---|---|---|---|---|---|
| 1 | | $H_2PtCl_6$ | 0.1 | No change | No change | No change | No Change | No Change | No Change |
| 2 | | ↑ | 0.2 | ↑ | ↑ | ↑ | ↑ | ↑ | ↑ |
| 3 | | ↑ | 1.0 | ↑ | ↑ | ↑ | ↑ | ↑ | ↑ |
| 4 | | ↑ | 2.0 | ↑ | ↑ | ↑ | ↑ | ↑ | ↑ |
| 5 | | ↑ | 5.0 | ↑ | ↑ | ↑ | ↑ | ↑ | ↑ |
| 6 | | ↑ | 8.0 | Some deterioration in response | Some shift to lean side | 2nd protective layer partly peeled off | ↑ | ↑ | 2nd protective layer partly peeled off |
| 7 | | Pt black | 1.0 | No change | No change | No change | ↑ | ↑ | No change |
| *8 | | ↑ | 5.0 | ↑ | ↑ | 2nd protective layer partly peeled off | ↑ | ↑ | 2nd protective layer partly peeled off |
| *9 | Step 5 omitted | $H_2PtCl_6$ | 1.0 | Little change | Little change | 1st protective layer partly peeled off | ↑ | ↑ | No change |
| *10 | Steps 5 and 9 omitted | ↑ | 1.0 | ↑ | ↑ | ↑ | ↑ | Some shift to lean side | ↑ |
| *11 | Steps 5 and 10 omitted | — | — | Deterioration in output | Some shift to lean side | 1st protective layer peeled off | Some deterioration in output | Shift to lean side | 1st protective layer partly broken |
| *12 | Step 9 omitted | $H_2PtCl_6$ | 0.1 (g/l) | No change | Shift to lean side | No change | No change | Shift to lean side | No change |

*Comparative Samples

TABLE 2-2

| Sample No. | Existence of steps | Carried amount of catalyst 1st protective layer (wt %) | Carried amount of catalyst 2nd protective layer (mole %) | Before durability test Item D | After durability test Item B | After durability test Item C |
|---|---|---|---|---|---|---|
| 13 | | 0 | 0.1 | Excellent | Some shift to lean side | No change |
| 14 | | 0.01 | 0.5 | ↑ | No change | ↑ |
| 15 | | 0.1 | 0.5 | ↑ | ↑ | ↑ |
| 16 | | 1 | 0.5 | ↑ | ↑ | ↑ |
| 17 | | 5 | 0.5 | Control Hz a little small | Some shift to lean side | Protective layer broken |
| *18 | Step 5 omitted | 0.5 | 0.5 | Excellent | Output width small, and considerable shift to rich side | Protective layer peeled off |

*Comparative Samples

What is claimed is:

at least a part, including at least a surface layer, of said porous protective layer comprises a granular mixture made up of grains formed substantially of a nonstoichiometric compound of a transition metal oxide, as defined in the International Periodic Table, said grains making up the granular mixture have a grain size of 0.1 to 0.5 μm, and a catalyst for causing reaction with the gas to be measured is carried in at least a part, including at least a surface layer, of the porous protective layer.

2. An oxygen-sensor element comprising a reference electrode on the side of one surface of a solid-electrolyte body and a measuring electrode on the side of another surface, for detecting an oxygen concentration of a gas to be measured, wherein the solid-electrolyte body comprises a base portion, a protruded portion with protrusions directly connected to the base portion, and the measuring electrode at a position including the protruded portion, the measuring electrode is coated with a porous first protective layer, which is coated with a porous second protective layer, and each of the first and second protective layers carries a noble-metal catalyst for promoting the oxidation reaction of the gas to be measured, the first protective layer comprises a metal oxide which is chemically stable against the gas to be measured, and the second protective layer comprises a nonstoichiometric transition metal oxide, as defined in the International Periodic Table.

3. An oxygen-sensor element comprising a reference electrode on the side of one surface of a solid-electrolyte body and a measuring electrode on the side of another surface, for detecting an oxygen concentration in a gas to be measured, wherein the solid-electrolyte body comprises a base portion and a protruded portion with protrusions connected to the base portion, the measuring electrode is coated with a porous first protective layer, which is coated with a porous second protective layer, and each of the first and second protective layers carries a noble-metal catalyst for promoting the oxidation reaction of the gas to be measured, the first protective layer is formed of a metal oxide which is chemically stable against the gas to be measured, and the second protective layer is formed of a nonstoichiometric transition-metal oxide, as defined in the International Periodic Table.

4. An oxygen-sensor element comprising a reference electrode on the side of one surface of a solid-electrolyte body and a measuring electrode on the side of another surface, for detecting an oxygen concentration of a gas to be measured, wherein the solid-electrolyte body comprises a base portion, a protruded portion with protrusions directly connected to the base portion and the measuring electrode at a position including the protruded portion, and the measuring electrode is coated with a porous protective layer, and at least a part of the protective layer is formed of a nonstoichiometric transition-metal oxide as defined in the International Periodic Table and carries a noble-metal catalyst for promoting the oxidation reaction of the gas to be measured.

5. An oxygen-sensor element comprising a reference electrode on the side of one surface of a solid-electrolyte body and a measuring electrode at the side of another surface, for detecting an oxygen density of a gas to be measured, wherein the solid-electrolyte body comprises a base portion and a protruded portion with protrusions connected to the base portion, and the measuring electrode is coated with a first porous protective layer which is covered with at least in part a second protective layer formed of a nonstoichiometric transition metal oxide as defined in the International Period Table and carries a noble-metal catalyst for promoting the oxidation reaction of the gas to be measured.

6. An oxygen-sensor element according to any one of claims 2-5, wherein said protrusions are generally spherical.

7. An oxygen-sensor element according to one of claims 1-5, wherein the transition metal oxide is titanium suboxide.

8. An oxygen-sensor element according to claim 7, wherein the titanium suboxide is represented by $TiO_x$, where $1.8 \leq x < 2$.

9. An oxygen-sensor according to claim 8, wherein the titanium suboxide is contained in an amount not less than 50 wt % of the porous protective layer comprising said nonstoichiometric transition metal oxide.

10. Any oxygen-sensor element according to claim 2 or 3, wherein the amount of the catalyst carried in the second protective layer is 0.02–5 mole %, relative to the material of the second protective layer.

11. An oxygen-sensor element according to claim 2, further comprising a heater for heating at least a portion relating to the detection function in the element.

12. An oxygen-sensor element according to any one of claims 1, 3, 4 and 5, further comprising a heater for heating at least a portion relating to the detection function in the element.

13. The oxygen sensor element according to claim 11 or 12, wherein said sensor element has a stability defined in terms of reduction in shift amount of the control point λ so that said control point λ fluctuates through a range of less than 0.001 between a value of the initial measurement and a value obtained when the oxygen sensor element is test mounted on an engine of a car after a durability test having a combustion gas temperature of not less than 450° C. or up to 400° C. at a constant driving speed of 80 km/hr under a lean control for a run distance of 80 kilometers.

14. An oxygen-sensor element according to one of claims 1-5, wherein the transition metal oxide consists of at least one oxide selected from the group consisting of oxides of Ti, Co and Ni.

15. An oxygen-sensor element according to claim 1, wherein said part of the protective layer formed mainly of the nonstoichiometric component has a thickness of 5–60 μm.

16. An oxygen-sensor element according to claim 1 or 15, wherein the surface layer having said granular texture extends within a range of 3/5–9/10 of the total length of the detection-gas-side of the solid-electrolyte body from a distal end thereof.

17. An oxygen-sensor element according to claim 1, wherein the porous protective layer contains 0.2–5 mole % of the catalyst.

18. An oxygen-sensor element according to claim 1, wherein the porous protective layer comprises a first inner protective layer and a second surface protective layer, said second surface protective layer having a granular texture made of granules and carrying the catalyst in the second surface protective layer.

19. An oxygen-sensor element according to claim 1, wherein the porous protective layer covers at least part of the surface of the solid-electrolyte body at least partially via a protruded portion on said body.

20. An oxygen-sensor element according to claim 1, wherein the surface layer is formed of titanium suboxide having an average crystal grain size of about 0.3 $\mu$m.

21. An oxygen-sensor element according to claim 1, wherein the surface layer has pores having an average pore size of about 0.1 $\mu$m.

22. An oxygen-sensor element according to any one of claims 2–5, wherein the average diameter of the protrusions is 40–100 $\mu$m.

23. An oxygen-sensor element according to claim 22, wherein the average diameter of the protrusions is 50–80 $\mu$m.

24. An oxygen-sensor element according to claim 2, 3 or 5, wherein the first protective layer has a porosity of 5–20%, and a thickness of 100–180 $\mu$m.

25. An oxygen-sensor element according to claim 24, wherein the second protective layer has a thickness thinner than that of the first protective layer.

26. An oxygen-sensor element according to claim 24, wherein the second protective layer has a thickness of 10–50 $\mu$m.

27. An oxygen-sensor element according to claim 2, 3 or 5, wherein the first protective layer is made of a material selected from the group consisting of $Al_2O_3$, spinel, BeO, $ZrO_2$ and mixtures of these materials.

28. An oxygen-sensor element according to claim 2, 3 or 5, wherein the first protective layer covers a distal end portion of the measuring electrode and a rear portion of the measuring electrode, and the first protective layer covering the distal end portion of the measuring electrode is not more than twice as thick as the first protective layer covering the rear portion of the measuring electrode.

29. An oxygen-sensor element according to claim 28, wherein the distal end portion of the element is thicker than the remaining portion of the element and extends over a length of 1/5–1/2 of the length in an axial direction from the distal end of the elements toward the mounting portion of the element.

30. An oxygen-sensor element according to claim 2, 3 or 5, wherein the noble-metal catalyst is present in the first protective layer in an amount of 0.01–5 wt %.

31. An oxygen-sensor element according to claim 30, wherein the content of the noble-metal catalyst in the first protective layer is not more than 1 wt %.

32. An oxygen-sensor element according to claim 2, 3 or 5, wherein the second protective layer has a porosity which is larger than that of the first protective layer.

33. An oxygen-sensor element according to claim 2, 3 or 5, wherein the second protective layer has a porosity of 8–15%.

34. An oxygen-sensor element according to claim 2, 3 or 5, wherein the first protective layer is formed by plasma flame spraying.

35. An oxygen-sensor element according to claim 2, 3 or 5, wherein the second protective layer is a fired layer of a coating layer on the first protective layer of a substance which is provided by mixing a protective-layer material and the noble-metal catalyst.

36. An oxygen-sensor element according to claim 35, wherein the protective-layer as the second protective layer is made of a powder having an average particle size of not more than 2 $\mu$m.

37. An oxygen-sensor element according to claim 4 or 5 wherein the amount of the catalyst carried in the protective layer formed of the nonstoichiometric transition metal oxide is 0.02 to 5 mole % based on the noble metal.

38. An oxygen-sensor element according to claim 1 or 4, wherein the protective layer has a porosity of 5–20%, and a thickness of 100–180 $\mu$m.

39. An oxygen-sensor element according to claim 1 or 4, wherein the porous protective layer includes a material selected from the group consisting of $Al_2O_3$, spinel, BeO, $ZrO_2$ and mixtures thereof.

40. An oxygen-sensor element according to claim 1 or 4, wherein the porous protective layer covers a distal end portion of the measuring electrode and a rear portion of the measuring electrode, and the first protective layer covering the distal end portion of the measuring electrode is not more than twice as thick as the first protective layer covering the rear portion of the measuring electrode.

41. An oxygen-sensor element according to claim 40, wherein the distal end portion of the element is thicker than the rear portion of the measuring electrode and the distal end portion extends over 1/5 to ½ of the measuring electrode in an axial direction from the distal end portion toward the rear portion of the measuring electrode.

42. An oxygen-sensor element according to claim 1 or 4, wherein the nonstoichiometric compound of the transition metal oxide is titanium suboxide contained in an amount of less than 50 wt % of said part of the porous protective layer exclusive of the catalyst.

43. An oxygen-sensor element according to claim 1 or 4, wherein said part of the porous protective layer has been fired from a green coating layer of a paste-like substance which is provided by mixing a protective-layer material and the catalyst.

44. The oxygen sensor according to claim 4, wherein said part of the protective layer formed of the nonstoichiometric transition-metal oxide has a granular texture, with grains of the nonstoichiometric transition-metal oxide making up a granule of the granular texture, and having a grain size of 0.1 to 0.5 $\mu$m.

45. The oxygen sensor according to claim 2, 3 or 5, wherein said nonstoichiometric transition metal oxide forms a granular texture, with grains of the nonstoichiometric transition-metal oxide making up a granule of the granular texture, and having a grain size of 0.1 to 0.5 $\mu$m.

46. The oxygen sensor element according to any one of claims 1–5, wherein said nonstoichiometric compound has a nonstoichiometry sufficient to perform oxidation reaction of gas components within a detection gas in cooperation with the catalyst.

47. The oxygen sensor element according to claim 46, wherein said nonstoichiometric compound comprises $TiO_x$ where x is from 1.8 to less than 2.

48. The oxygen sensor element according to any one of claim 1–5, wherein said sensor element has a stable control point $\lambda$ of excess air factor in terms of fall down time Tdw between an initial measurement and a measurement after a durability test which fluctuates through a range of less than 0.001.

49. The oxygen sensor element according to claim 48, wherein said stability is defined in terms of reduction in shift amount of the control point λ between a value of the initial measurement and a value obtainable when the oxygen sensor element is tested after a durability test under the conditions of a combustion gas temperature of 700° to 850° C. at an air-to-fuel ratio of 10 for 200 hours.

50. The oxygen sensor element according to claim 49, wherein said stability is defined by a ratio T where $T=Tdw/(Tup+Tdw)$ and is less than 0.44, and where Tdw represents a lapse of time from a time gas is changed to lean until the sensor reaches a reference voltage, and Tup represents a lapse of time from a time gas is changed to rich until the sensor reaches a reference voltage.

51. The oxygen sensor element according to claim 50, wherein said stability is additionally defined by a difference in the ratio T of a T-ratio measured at initial time of testing from a T- ratio measured after the durability test, said difference being smaller than 0.02.

52. An oxygen sensor which comprises the oxygen sensor element as defined in claim 49.

53. An exhaust gas purification system which comprises the oxygen sensor as defined in claim 52.

54. A combustion engine which comprises the oxygen sensor as defined in claim 52.

55. A car which comprises the engine as defined in claim 54.

* * * * *

UNITED STATES PATENT AND TRADEMARK OFFICE
CERTIFICATE OF CORRECTION

PATENT NO. : 5,443,711
DATED : August 22, 1995
INVENTOR(S) : Takao Kojima, et. al.

It is certified that error appears in the above-indentified patent and that said Letters Patent is hereby corrected as shown below:

At the top of column 25, please add the following:

1.  An oxygen-sensor element comprising a reference-gas-side electrode on one surface of a solid-electrolyte body, a detection-gas-side electrode on another surface, and a porous protective layer on the surface of said detection-gas-side electrode, for measuring oxygen concentration of a gas to be measured using an electromotive force produced in accordance with a difference in oxygen concentration between the reference-gas-side and the detection-gas side, wherein Signed and Sealed this Fourth Day of June, 1996

Attest:

BRUCE LEHMAN

Attesting Officer        Commissioner of Patents and Trademarks